US007226978B2

(12) United States Patent
Tapsak et al.

(10) Patent No.: US 7,226,978 B2
(45) Date of Patent: *Jun. 5, 2007

(54) TECHNIQUES TO IMPROVE POLYURETHANE MEMBRANES FOR IMPLANTABLE GLUCOSE SENSORS

(75) Inventors: Mark A. Tapsak, San Diego, CA (US); Rathbun K. Rhodes, Madison, WI (US); Mark C. Shults, Madison, WI (US); Jason D. McClure, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/153,356

(22) Filed: May 22, 2002

(65) Prior Publication Data
US 2003/0217966 A1 Nov. 27, 2003

(51) Int. Cl.
*C08F 265/10* (2006.01)
*B01D 39/14* (2006.01)
(52) U.S. Cl. ............ 525/296; 210/500.21; 210/500.27; 210/500.34; 424/424; 525/420; 525/424; 525/440; 525/452; 525/453; 525/474; 604/891.1
(58) Field of Classification Search ................ 525/296, 525/420, 424, 440, 452, 453, 474; 210/500.21, 210/500.27, 500.34; 424/424; 604/891.1
See application file for complete search history.

(56) References Cited

U.S. PATENT DOCUMENTS

| 3,775,182 A | 11/1973 | Patton et al. |
| 3,929,971 A | 12/1975 | Roy |
| 3,966,580 A | 6/1976 | Janata et al. |
| 3,979,274 A | 9/1976 | Newman |
| 4,040,908 A | 8/1977 | Clark |
| 4,073,713 A | 2/1978 | Newman |
| 4,076,656 A | 2/1978 | White et al. |
| 4,172,770 A | 10/1979 | Semersky et al. |
| 4,197,840 A | 4/1980 | Beck et al. |
| 4,240,889 A | 12/1980 | Yoda et al. |
| 4,255,500 A | 3/1981 | Hooke |
| 4,353,888 A | 10/1982 | Sefton |
| 4,374,013 A | 2/1983 | Enfors |
| 4,388,166 A | 6/1983 | Suzuki et al. |
| 4,415,666 A | 11/1983 | D'Orazio et al. |
| 4,418,148 A | 11/1983 | Oberhardt |
| 4,431,004 A | 2/1984 | Bessman et al. |
| 4,436,094 A | 3/1984 | Cerami |
| 4,484,987 A | 11/1984 | Gough |
| 4,506,680 A | 3/1985 | Stokes |
| 4,534,355 A | 8/1985 | Potter |
| 4,577,642 A | 3/1986 | Stokes |
| 4,650,547 A | 3/1987 | Gough |
| 4,671,288 A | 6/1987 | Gough |
| 4,686,044 A | 8/1987 | Behnke et al. |
| 4,689,309 A | 8/1987 | Jones |
| 4,702,732 A | 10/1987 | Powers et al. |
| 4,703,756 A | 11/1987 | Gough et al. |
| 4,711,251 A | 12/1987 | Stokes |
| 4,753,652 A | 6/1988 | Langer et al. |
| 4,757,022 A | 7/1988 | Shults et al. |
| 4,759,828 A | 7/1988 | Young et al. |
| 4,776,944 A | 10/1988 | Janata et al. |
| 4,781,798 A | 11/1988 | Gough |
| 4,803,243 A | 2/1989 | Fujimoto et al. |
| 4,810,470 A | 3/1989 | Burkhardt et al. |
| 4,861,830 A | 8/1989 | Ward |
| 4,871,440 A | 10/1989 | Nagata et al. |
| 4,889,744 A | 12/1989 | Quaid |
| 4,890,620 A | 1/1990 | Gough |
| 4,927,407 A | 5/1990 | Dorman |
| 4,935,345 A | 6/1990 | Guilbeau et al. |
| 4,963,595 A | 10/1990 | Ward et al. |
| 4,984,929 A | 1/1991 | Rock et al. |
| 4,986,671 A | 1/1991 | Sun et al. |
| 4,994,167 A | 2/1991 | Shults et al. |
| 5,002,572 A | 3/1991 | Picha |

(Continued)

FOREIGN PATENT DOCUMENTS

| EP | 0107634 | 5/1984 |
| EP | 0 534 074 | 3/1993 |
| EP | 0535898 | 4/1993 |
| EP | 0885932 | 12/1998 |
| EP | 0817809 | 7/2002 |

(Continued)

OTHER PUBLICATIONS

Hawley's Condensed Chemical Dictionary (14th Edition), John Wiley & Sons, Richard J. Lewis, Sr., p. 1248.*
Atanasov, et al. Biosensor for Continuous Glucose Monitoring. Biotechnology and Bioengineering 1994, 43, 262-266.
Baker, et al. Dynamic concentration challenges for biosensor characterization. Biosens Bioelectron 1993, 8, 433-441.
Bani Amer, M. M. An accurate amperometric glucose sensor based glucometer with eliminated cross-sensitivity. J Med Eng Technol 2002, 26, 208-13.

(Continued)

Primary Examiner—John M. Cooney, Jr.
(74) Attorney, Agent, or Firm—Knobbe Martens Olson & Bear LLP

(57) ABSTRACT

The invention provides an implantable membrane for regulating the transport of analytes therethrough that includes a matrix including a first polymer; and a second polymer dispersed throughout the matrix, wherein the second polymer forms a network of microdomains which when hydrated are not observable using photomicroscopy at 400× magnification or less. In one aspect, the homogeneous membrane of the present invention has hydrophilic domains dispersed substantially throughout a hydrophobic matrix to provide an optimum balance between oxygen and glucose transport to an electrochemical glucose sensor.

6 Claims, 7 Drawing Sheets

U.S. PATENT DOCUMENTS

| | | |
|---|---|---|
| 5,007,929 A | 4/1991 | Quaid |
| 5,059,654 A | 10/1991 | Hou et al. |
| 5,101,814 A | 4/1992 | Palti |
| 5,113,871 A | 5/1992 | Viljanto et al. |
| 5,165,407 A | 11/1992 | Wilson et al. |
| 5,171,689 A | 12/1992 | Kawaguri et al. |
| 5,190,041 A | 3/1993 | Palti |
| 5,235,003 A | 8/1993 | Ward et al. |
| 5,271,736 A | 12/1993 | Picha |
| 5,282,848 A | 2/1994 | Schmitt |
| 5,314,471 A | 5/1994 | Brauker et al. |
| 5,322,063 A | 6/1994 | Allen et al. |
| 5,326,356 A | 7/1994 | Della Valle et al. |
| 5,340,352 A | 8/1994 | Nakanishi et al. |
| 5,344,454 A | 9/1994 | Clarke et al. |
| 5,348,788 A | 9/1994 | White |
| 5,356,786 A | 10/1994 | Heller et al. |
| 5,372,133 A | 12/1994 | Hogen Esch |
| 5,380,536 A | 1/1995 | Hubbell et al. |
| 5,384,028 A | 1/1995 | Ito |
| 5,391,250 A | 2/1995 | Cheney et al. |
| 5,397,848 A | 3/1995 | Yang et al. |
| 5,428,123 A | 6/1995 | Ward et al. |
| 5,431,160 A | 7/1995 | Wilkins |
| 5,453,278 A | 9/1995 | Chan et al. |
| 5,462,064 A | 10/1995 | D'Angelo et al. |
| 5,469,846 A | 11/1995 | Khan |
| 5,476,094 A | 12/1995 | Allen et al. |
| 5,496,453 A | 3/1996 | Uenoyama et al. |
| 5,531,878 A | 7/1996 | Vadgama et al. |
| 5,540,828 A | 7/1996 | Yacynych |
| 5,545,220 A | 8/1996 | Andrews et al. |
| 5,545,223 A | 8/1996 | Neuenfeldt et al. |
| 5,549,675 A | 8/1996 | Neuenfeldt et al. |
| 5,564,439 A | 10/1996 | Picha |
| 5,569,186 A | 10/1996 | Lord et al. |
| 5,569,462 A | 10/1996 | Martinson et al. |
| 5,571,395 A | 11/1996 | Park et al. |
| 5,575,930 A | 11/1996 | Tietje-Girault et al. |
| 5,584,876 A | 12/1996 | Bruchman et al. |
| 5,589,563 A | 12/1996 | Ward et al. |
| 5,593,440 A | 1/1997 | Brauker et al. |
| 5,593,852 A | 1/1997 | Heller et al. |
| 5,628,890 A | 5/1997 | Carter et al. |
| 5,653,756 A | 8/1997 | Clarke et al. |
| 5,653,863 A | 8/1997 | Genshaw et al. |
| 5,658,330 A | 8/1997 | Carlisle et al. |
| 5,683,562 A | 11/1997 | Schaffar et al. |
| 5,686,829 A | 11/1997 | Girault |
| 5,706,807 A | 1/1998 | Picha |
| 5,711,861 A | 1/1998 | Ward et al. |
| 5,713,888 A | 2/1998 | Neuenfeldt et al. |
| 5,733,336 A | 3/1998 | Neuenfeldt et al. |
| 5,741,330 A | 4/1998 | Brauker et al. |
| 5,756,632 A | 5/1998 | Ward et al. |
| 5,776,324 A | 7/1998 | Usala |
| 5,777,060 A | 7/1998 | Van Antwerp |
| 5,782,912 A | 7/1998 | Brauker et al. |
| 5,783,054 A | 7/1998 | Raguse et al. |
| 5,787,900 A | 8/1998 | Butler et al. |
| 5,791,344 A | 8/1998 | Schulman et al. |
| 5,795,774 A | 8/1998 | Matsumoto et al. |
| 5,798,065 A | 8/1998 | Picha |
| 5,800,529 A | 9/1998 | Brauker et al. |
| 5,807,406 A | 9/1998 | Brauker et al. |
| 5,811,487 A | 9/1998 | Schulz, Jr. et al. |
| 5,833,603 A | 11/1998 | Kovacs et al. |
| 5,837,728 A | 11/1998 | Purcell |
| 5,840,240 A | 11/1998 | Stenoien et al. |
| 5,861,019 A | 1/1999 | Sun et al. |
| 5,871,514 A | 2/1999 | Wiklund et al. |
| 5,882,494 A | 3/1999 | Van Antwerp |
| 5,897,578 A | 4/1999 | Wiklund et al. |
| 5,904,708 A | 5/1999 | Goedeke |
| 5,910,554 A | 6/1999 | Kempe et al. |
| 5,913,998 A | 6/1999 | Butler et al. |
| 5,914,026 A | 6/1999 | Blubaugh, Jr. et al. |
| 5,919,215 A | 7/1999 | Wiklund et al. |
| 5,964,261 A | 10/1999 | Neuenfeldt et al. |
| 5,964,804 A | 10/1999 | Brauker et al. |
| 5,964,993 A | 10/1999 | Blubaugh et al. |
| 5,965,380 A | 10/1999 | Heller et al. |
| 5,976,085 A | 11/1999 | Kimball et al. |
| 5,985,129 A | 11/1999 | Gough et al. |
| 5,999,848 A | 12/1999 | Gord et al. |
| 6,001,067 A | 12/1999 | Shults et al. |
| 6,007,845 A * | 12/1999 | Domb et al. ................ 424/501 |
| 6,011,984 A | 1/2000 | Van Antwerp et al. |
| 6,013,113 A | 1/2000 | Mika |
| 6,016,448 A | 1/2000 | Busacker et al. |
| 6,049,727 A | 4/2000 | Crothall |
| 6,063,637 A | 5/2000 | Arnold et al. |
| 6,071,406 A * | 6/2000 | Tsou ................... 210/500.41 |
| 6,081,736 A | 6/2000 | Colvin et al. |
| 6,083,710 A | 7/2000 | Heller et al. |
| 6,088,608 A | 7/2000 | Schulman et al. |
| 6,119,028 A | 9/2000 | Schulman et al. |
| 6,135,978 A | 10/2000 | Houben et al. |
| 6,144,869 A | 11/2000 | Berner et al. |
| 6,162,611 A | 12/2000 | Heller et al. |
| 6,175,752 B1 | 1/2001 | Say et al. |
| 6,187,062 B1 | 2/2001 | Oweis et al. |
| 6,200,772 B1 | 3/2001 | Vadgama et al. |
| 6,201,980 B1 | 3/2001 | Darrow et al. |
| 6,208,894 B1 | 3/2001 | Schulman et al. |
| 6,212,416 B1 | 4/2001 | Ward et al. |
| 6,230,059 B1 | 5/2001 | Duffin |
| 6,231,879 B1 | 5/2001 | Li et al. |
| 6,233,471 B1 | 5/2001 | Berner et al. |
| 6,241,863 B1 | 6/2001 | Monbouquette |
| 6,248,067 B1 | 6/2001 | Causey, III et al. |
| 6,256,522 B1 | 7/2001 | Schultz |
| 6,259,937 B1 | 7/2001 | Schulman et al. |
| 6,274,285 B1 | 8/2001 | Gries et al. |
| 6,275,717 B1 | 8/2001 | Gross et al. |
| 6,284,478 B1 | 9/2001 | Heller et al. |
| 6,299,578 B1 | 10/2001 | Kurnik et al. |
| 6,300,002 B1 | 10/2001 | Webb et al. |
| 6,309,351 B1 | 10/2001 | Kurnik et al. |
| 6,309,384 B1 | 10/2001 | Harrington et al. |
| 6,325,978 B1 | 12/2001 | Labuda et al. |
| 6,325,979 B1 | 12/2001 | Hahn et al. |
| 6,329,161 B1 | 12/2001 | Heller et al. |
| 6,330,464 B1 | 12/2001 | Colvin, Jr. et al. |
| 6,365,670 B1 | 4/2002 | Fry |
| 6,372,244 B1 | 4/2002 | Antanavich et al. |
| 6,400,974 B1 | 6/2002 | Lesho |
| 6,409,674 B1 | 6/2002 | Brockway et al. |
| 6,447,448 B1 | 9/2002 | Ishikawa et al. |
| 6,447,542 B1 | 9/2002 | Weadock |
| 6,454,710 B1 | 9/2002 | Ballerstadt et al. |
| 6,459,917 B1 | 10/2002 | Gowda et al. |
| 6,461,496 B1 | 10/2002 | Feldman et al. |
| 6,466,810 B1 | 10/2002 | Ward et al. |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,514,718 B2 | 2/2003 | Heller et al. |
| 6,520,997 B1 | 2/2003 | Pekkarinen et al. |
| 6,527,729 B1 | 3/2003 | Turcott |
| 6,537,318 B1 | 3/2003 | Ita et al. |
| 6,541,107 B1 | 4/2003 | Zhong et al. |
| 6,545,085 B2 | 4/2003 | Kilgour et al. |

| | | |
|---|---|---|
| 6,546,268 B1 | 4/2003 | Ishikawa et al. |
| 6,547,839 B2 | 4/2003 | Zhang et al. |
| 6,551,496 B1 | 4/2003 | Moles et al. |
| 6,558,321 B1 | 5/2003 | Burd et al. |
| 6,579,498 B1 | 6/2003 | Eglise |
| 6,615,078 B1 | 9/2003 | Burson et al. |
| 6,618,934 B1 | 9/2003 | Feldman et al. |
| 6,702,857 B2 | 3/2004 | Brauker et al. |
| 6,721,587 B2 * | 4/2004 | Gough .................. 600/345 |
| 6,741,877 B1 | 5/2004 | Shults et al. |
| 2002/0022883 A1 | 2/2002 | Burg |
| 2002/0042090 A1 | 4/2002 | Heller et al. |
| 2002/0151796 A1 | 10/2002 | Koulik |
| 2002/0182241 A1 | 12/2002 | Boerenstein et al. |
| 2002/0193885 A1 | 12/2002 | Legeay et al. |
| 2003/0006669 A1 | 1/2003 | Pei et al. |
| 2003/0023317 A1 | 1/2003 | Brauker et al. |
| 2003/0032874 A1 | 2/2003 | Rhodes et al. |
| 2003/0036803 A1 | 2/2003 | McGhan et al. |
| 2003/0070548 A1 | 4/2003 | Clausen |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0091433 A1 | 5/2003 | Tam et al. |
| 2003/0125613 A1 | 7/2003 | Enegren et al. |
| 2003/0217966 A1 | 11/2003 | Tapsak et al. |
| 2004/0011671 A1 | 1/2004 | Shults et al. |
| 2004/0045879 A1 | 3/2004 | Shults et al. |
| 2004/0106857 A1 | 6/2004 | Gough |
| 2004/0186362 A1 | 9/2004 | Brauker et al. |
| 2004/0199059 A1 | 10/2004 | Brauker et al. |

FOREIGN PATENT DOCUMENTS

| | | |
|---|---|---|
| FR | 2 656 423 | 6/1991 |
| FR | 2760962 | 9/1998 |
| GB | 1442303 | 7/1976 |
| JP | 62083849 | 4/1987 |
| WO | WO9000738 | 1/1990 |
| WO | WO9207525 | 5/1992 |
| WO | WO9213271 | 8/1992 |
| WO | WO9319701 | 10/1993 |
| WO | WO9601611 | 1/1996 |
| WO | WO9630431 | 10/1996 |
| WO | WO9632076 | 10/1996 |
| WO | WO9636296 | 11/1996 |
| WO | WO 97/43633 | 11/1997 |
| WO | WO 98/24358 | 6/1998 |
| WO | WO 00/13003 | 3/2000 |
| WO | WO0019887 | 4/2000 |
| WO | WO 00/32098 | 6/2000 |
| WO | WO0033065 | 6/2000 |
| WO | WO 00/59373 | 10/2000 |
| WO | WO 01/12158 | 2/2001 |
| WO | WO0120019 | 3/2001 |
| WO | WO0120334 | 3/2001 |
| WO | WO 01/43660 | 6/2001 |
| WO | WO0158348 | 8/2001 |
| WO | WO0188524 | 11/2001 |
| WO | WO02053764 | 7/2002 |

OTHER PUBLICATIONS

Beach, et al. Subminiature implantable potentiostat and modified commerical telemetry device for remote glucose monitoring. IEEE Transactions on Instrumentation and Measurement 1999, 48, 1239-1245.

Bindra, et al. Pulsed amperometric detection of glucose in biological fluids at a surface-modified gold electrode. Anal Chem 1989, 61, 2566-2570.

Bode, B. W. Clinical utility of the continuous glucose monitoring system. Diabetes Technol Ther 2000, 2 Suppl 1, S35-41.

Bode, et al. Continuous glucose monitoring used to adjust diabetes therapy improves glycosylated hemoglobin: a pilot study. Diabetes Res Clin Pract 1999, 46, 183-190.

Bode, et al. Using the continuous glucose monitoring system to improve the management of type 1 diabetes. Diabetes Technol Ther 2000, 2 Suppl 1, S43-8.

Bott A. W. A Comparison of Cyclic Voltammetryand Cyclic Staircase Voltammetry. Current Separations 1997, 16:1, 23-26.

Brauker, J.H. Unraveling Mysteries at the Biointerface: Molecular Mediator of Inhibition of Blood Vessel Formation in the Foreign Body Capsule Revealed. Surfacts Biomaterials 2001,6, 1;5.

Brauker, et al. Neovascularization of synthetic membranes directed by membrane microarchitecture. J Biomed Mater Res 1995, 29, 1517-1524.

Brauker, et al. Sustained expression of high levels of human factor IX from human cells implanted within an immunoisolation device into athymic rodents. Hum Gene. Ther 1998, 9, 879-888.

Bremer, et al. Benchmark data from the literature for evaluation of new glucose sensing technologies. Diabetes Technol Ther 2001, 3, 409-418.

Brunner, et al. Validation of home blood glucose meters with respect to clinical and analytical approaches. Diabetes Care 1998, 21, 585-590.

D'Arrigo, et al. Porous-Si based bioreactors for glucose monitoring and drugs production. Proc. of SPIE 2003, 4982, 178-184.

Dixon, et al. Characterization in vitro and in vivo of the oxygen dependence of an enzyme/polymer biosensor for monitoring brain glucose. J Neurosci Methods 2002, 119, 135-142.

Ernst, et al. Reliable glucose monitoring through the use of microsystem technology. Anal Bioanal Chem 2002, 373, 758-761.

Fare, et al. Functional characterization of a conducting polymer-based immunoassay system. Biosens Bioelectron 1998, 13, 459-470.

Frost, et al. Implantable chemical sensors for real-time clinical monitoring: progress and challenges. Curr Opin Chem Biol 2002, 6, 633-641.

Geller, et al. Use of an Immunoisolation device for cell transplantation and tumor immunotherapy. Ann NY Acad Sci 1997, 831, 438-451.

Gerritsen, M. Problems associated with subcutaneously implanted glucose sensors. Diabetes Care 2000, 23, 143-5.

Gerritsen, et al. Influence of inflammatory cells and serum on the performance of implantable glucose sensors. J Biomed Mater Res 2001, 54, 69-75.

Gerritsen, et al. Performance of subcutaneously implanted glucose sensors for continuous monitoring. Neth J Med 1999, 54, 167-179.

Gilligan, et al. Evaluation of a subcutaneous glucose sensor out to 3 months in a dog model. Diabetes Care 1994, 17:8, 882-887.

Gough, et al. Immobilized glucose oxidase in implantable glucose sensor technology. Diabetes Technol Ther 2000, 2, 377-380.

Gross, et al. Performance evaluation of the MiniMed continuous glucose monitoring system during patient home use. Diabetes Technol Ther 2000, 2, 49-56.

Gross, et al. Efficacy and reliability of the continuous glucose monitoring system. Diabetes Technol Ther 2000, 2 Suppl 1, S19-26.

Hall, et al. Electrochemical oxidation of hydrogen peroxide at platinum electrodes. Part 1. An adsorption-controlled mechanism. Electrochimica Acta 1998, 43, 579-588.

Hall, et al. Electrochemical oxidation of hydrogen peroxide at platinum electrodes. Part II: effect of potential. Electrochimica Acta 1998, 43, 2015-2024.

Hall, et al. Electrochemical oxidation of hydrogen peroxide at platinum electrodes. Part III: Effect of temperature. Electrochimica Acta 1999, 44, 2455-2462.

Hall, et al. Electrochemical oxidation of hydrogen peroxide at platinum electrodes. Part IV: phosphate buffer dependence. Electrochimica Acta 1999, 44, 4573-4582.

Hall, et al. Electrochemical oxidation of hydrogen peroxide at platinum electrodes. Part V: inhibition by chloride. Electrochimica Acta 2000, 45, 3573-3579.

Hitchman, M. Measurement of Dissolved Oxygen. Chemical Analysis 1978, 49, 34-123.

Ishikawa, et al. Initial evaluation of a 290-microm diameter subcutaneous glucose sensor: glucose monitoring with a biocompatible, flexible-wire, enzyme-based amperometric microsensor in diabetic and nondiabetic humans. J Diabetes Complications 1998, 12, 295-301.

Jensen, et al. Fast Wave Forms for Pulsed Electrochemical Detection of Glucose by Incorporation of Reduction Desorption of Oxidation Products. Analytical Chemistry 1997, 69, 1776-1781.

Johnson, et al. In vivo evaluation of an electroenzymatic glucose sensor implanted in subcutaneous tissue. Biosens Bioelectron 1992, 7, 709-714.

Jovanovic, L. The role of continuous glucose monitoring in gestational diabetes mellitus. Diabetes Technol Ther 2000, 2 Suppl 1, S67-71.

Kargol, et al. Studies on the structural properties of porous membranes: measurement of linear dimensions of solutes. Biophys Chem 2001, 91, 263-271.

Kaufman, F. R. Role of the continuous glucose monitoring system in pediatric patients. Diabetes Technol Ther 2000, 2 Suppl 1, S49-52.

Kiechle, F.L. The impact of continuous glucose monitoring on hospital point-of-care testing programs. Diabetes Technol Ther 2001, 3, 647-649.

Koschinsky, et al. Sensors for glucose monitoring: technical and clinical aspects. Diabetes Metab Res Rev 2001, 17, 113-123.

Kruger, et al. Psychological motivation and patient education: a role for continuous glucose monitoring. Diabetes Technol Ther 2000, 2 Suppl 1, S93-7.

Lee, et al. Effects of pore size, void volume, and pore connectivity on tissue responses. Society for Biomaterials 1999, 25$^{th}$ Annual Meeting, 171.

Lerner, et al. An implantable electrochemical glucose sensor. Ann N Y Acad Sci 1984, 428, 263-278.

Leypoldt, et al. Model of a two-substrate enzyme electrode for glucose. Anal Chem 1984, 56, 2896-2904.

Makale, et al. Tissue window chamber system for validation of implanted oxygen sensors. Am J Physiol Heart Circ Physiol 2003, 284, 1-24.

Maran, et al. Continuous subcutaneous glucose monitoring in diabetic patients: a multicenter anaylsis. Diabetes Care 2002, 25, 347-52.

Matsumoto, et al. A long-term lifetime amperometric glucose sensor with a perfluorocarbon polymer coating. Biosens Bioelectron 2001, 16, 271-276.

Miller, A. Human monocyte/macrophage activation and interleukin 1 generation by biomedical polymers. J Biomed Mater Res 1988, 23, 1007-1026.

Miller, et al. Generation of IL-1 like activity in response to biomedical polymer implants: a comparison of in vitro and in vivo models. J Biomed Mater Res 1989, 23, 911-930.

Miller, et al. In vitro stimulation of fibroblast activity by factors generated from human monocytes activated by biomedical polymers. Journal of J Biomed Mater Res 1989, 23, 911-930.

Moussy, et al. Biomaterials community examines biosensor biocompatibility. Diabetes Technol Ther 2000, 2, 473-477.

Mowery, et al. Preparation and characterization of hydrophobic polymeric films that are thromboresistant via nitric oxide release. Biomaterials 2000, 21, 9-21.

Myler, et al. Ultra-thin-polysiloxane-film-composite membranes for the optimisation of amperometric oxidase enzyme electrodes. Biosens Bioelectron 2002, 17, 35-43.

Nam, et al. A novel fabrication method of macroporous biodegradable polymer scaffolds using gas foaming salt as a porogen additive. J Biomed Mater Res 2000, 53, 1-7.

Palmisano, et al. Simultaneous monitoring of glucose and lactate by an interference and cross-talk free dual electrode amperometric biosensor based on electropolymerized thin films. Biosens Bioelectron 2000, 15, 531-539.

Pitzer, et al. Detection of hypoglycemia with the GlucoWatch biographer. Diabetes Care 2001, 24, 881-5.

Poltout, et al. A glucose monitoring system for on line estimation in man of blood glucose concentration using a miniaturized glucose sensor implanted in the subcutaneous tissue and a wearable control unit. Diabetologia 1993, 36, 658-663.

Postlethwaite, et al. Interdigitated Array Electrode as an Alternative to the Rotated Ring-Disk Electrode for Determination of the Reaction Products of Dioxygen Reduction. Analytical Chemistry 1996, 68, 2951-2958.

Ratner, B.D. Reducing capsular thickness and enhancing angiogenesis around implant drug release systems. J Control Release 2002, 78, 211-218.

Rhodes et al., Prediction of pocket-portable and implantable glucose enzyme electrode performance from combined species permeability and digital simulation analysis. Analytical Chemistry 1994, 66, 1520-1529.

Sansen, et al. A smart sensor for the voltammetric measurement of oxygen or glucose concentrations. Sensors and Actuators 1990, 1, 298-302.

Sansen, et al. "Glucose sensor with telemetry system." Ko, W.H. (Ed). Implantable Sensors for Closed Loop Prosthetic Systems, Ch. 12, 167-175, Futura Publishing Co. (1985).

Schmidt, et al. Glucose concentration in subcutaneous extracellular space. Diabetes Care 1993, 16, 695-700.

Schoemaker, et al. The SCGM1 System: Subcutaneous Continuous Glucose Monitoring Based on Microdialysis Technique. Diabetes Technol Ther 2003, 5, 599-608.

Shults, et al. A telemetry-instrumentation system for monitoring multiple subcutaneously implanted glucose sensors. IEEE Transactions on Biomedical Engineering 1994, 41, 937-942.

Sieminski, et al. Biomaterial-microvasculature interactions. Biomaterials 2000, 21, 2233-2241.

Skyler, J. S. The economic burden of diabetes and the benefits of improved glycemic control: the potential role of a continuous glucose monitoring system. Diabetes Technol Ther 2000, 2 Suppl 1, S7-12.

Steil, et al. Determination of plasma glucose during rapid glucose excursions with a subcutaneous glucose sensor. Diabetes Technol Ther 2003, 5, 27-31.

Tanenberg, et al. Continuous glucose monitoring system: a new approach to the diagnosis of diabetic gastroparesis. Diabetes Technol Ther 2000, 2 Suppl 1, S73-80.

Tang, et al. Fibrin(ogen) mediates acute inflammatory responses to biomaterials. J Exp Med 1993, 178, 2147-2156.

Tang, et al. Inflammatory responses to biomaterials. Am J Clin Pathol 1995, 103, 466-471.

Tang, et al. Mast cells mediate acute inflammatory responses to implanted biomaterials. Proc Natl Acad Sci U S A 1998, 95, 8841-8846.

Tang, et al. Molecular determinants of acute inflammatory responses to biomaterials. J Clin Invest 1996, 97, 1329-1334.

Thome-Duret, et. al. Modification of the sensitivity of glucose sensor implanted into subcutaneous tissue. Diabetes Metab 1996, 22, 174-178.

Tibell, et al. Survival of macroencapsulated allogeneic parathyroid tissue one year after transplantation in nonimmunosuppressed humans. Cell Transplant 2001, 10, 591-9.

Tierney, et al. The GlucoWatch biographer: a frequent automatic and noninvasive glucose monitor. Ann Med 2000, 32, 632-641.

Updike et al. Enzymatic glucose sensors: improved long-term performance in vitro and in vivo. ASAIO Journal 1994, 40, 157-163.

Updike et al. "Principles of long-term fully implanted sensors with emphasis on radiotelemetric monitoring of blood glucose from inside a subcutaneous foreign body capsule (FBC)." Fraser, D.M. (Ed.). Biosensors in the body: continuous in vivo monitoring. Chap. 4, pp. 117-137, John Wiley & Sons Ltd., (1997).

Updike, et al. A subcutaneous glucose sensor with improved longevity, dynamic range, and stability of calibration. Diabetes Care 2000, 23, 208-214.

Updike, et al. The enzyme electrode. Nature 1967, 214, 986-988.

Wagner, et al. A. Continuous amperometric monitoring of glucose in a brittle diabetic chimpanzee with a miniature subcutaneous electrode. Proc Natl Acad Sci U S A 1998, 95, 6379-6382.

Ward et al. A new amperometric microsensor: in vitro and short-term in vivo evaluation. Biosensors & Bioelectronics 2002, 17, 181-189.

Ward, et al., Rise in background current over time in a subcutaneous glucose sensor in the rabbit: relevance tp calibration and accuracy. Biosensors & Bioelectronics 2000, 15, 53-61.

Wu, et al. In situ electrochemical oxygen generation with an immunoisolation device. Ann N Y Acad Sci 1999, 875, 105-125.

Yang, et al. Development of needle-type glucose sensor with high selectivity. Science and Actuators B 1998, 46, 249-256.

International Search Report from PCT/US03/15816, Sep. 22, 2003.

Gross, Todd, "Letters to the Editor Re: Diabetes Technology & Therapeutics, 2000;2:49-56," vol. 3, No. 1, p. 130-131, 2001.

Huang, C., O'Grady, W.E.; Yeager, E. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116, Aug. 1975.

Malin, et al., "Noninvasive Prediction of Glucose by Near-Infrared Diffuse Reflectance Spectroscopy." Clinical Chemistry 1999, 45:9:1651-1658.

Reach, Gerard, "Letters to the Editor: Re: Diabetes Technology & Therapeutics, 2000;2:49-56," vol. 3, No. 1, p. 129-130, 2001.

Wilkins, E.; Atanasov, P.; Muggenburg, B. A., "Integrated implantable device for long-term glucose monitoring," Biosens Bioelectron 1995, 10, 485-494.

Wilson, et al. Enzyme-based biosensors for in vivo measurements. Chem Rev 2000, 100:2693-2704.

U.S. Appl. No. 10/789,359, filed Feb. 26, 2004.
U.S. Appl. No. 10/838,658, filed May 3, 2004.
U.S. Appl. No. 10/838,909, filed May 3, 2004.
U.S. Appl. No. 10/838,912, filed May 3, 2004.
U.S. Appl. No. 10/842,716, filed May 10, 2004.
U.S. Appl. No. 10/846,150, filed May 14, 2004.
U.S. Appl. No. 10/885,476, filed Jul. 6, 2004.
U.S. Appl. No. 10/896,637, filed Jul. 21, 2004.
U.S. Appl. No. 10/897,772, filed Jul. 21, 2004.
U.S. Appl. No. 10/896,639, filed Jul. 21, 2004.
U.S. Appl. No. 10/897,377, filed Jul. 21, 2004.
U.S. Appl. No. 10/896,312, filed Jul. 21, 2004.

* cited by examiner

TECHNIQUES TO IMPROVE POLYURETHANE MEMBRANES FOR IMPLANTABLE GLUCOSE SENSORS

FIELD OF THE INVENTION

The present invention relates generally to membranes for use in combination with implantable devices for evaluating an analyte in a body fluid. More particularly, the invention relates to membranes for controlling the diffusion of glucose therethrough to a glucose sensor.

BACKGROUND OF THE INVENTION

A biosensor is a device that uses biological recognition properties for the selective analysis of various analytes or biomolecules. Generally, the sensor will produce a signal that is quantitatively related to the concentration of the analyte. In particular, a great deal of research has been directed toward the development of a glucose sensor that would function in vivo to monitor a patient's blood glucose level. Such a glucose sensor is useful in the treatment of diabetes mellitus. In particular, an implantable glucose sensor that would continuously monitor the patient's blood glucose level would provide a physician with more accurate information in order to develop optimal therapy. One type of glucose sensor is the amperometric electrochemical glucose sensor. Typically, an electrochemical glucose sensor employs the use of a glucose oxidase enzyme to catalyze the reaction between glucose and oxygen and subsequently generate an electrical signal. The reaction catalyzed by glucose oxidase yields gluconic acid and hydrogen peroxide as shown in the reaction below (equation 1):

$$\text{glucose} + O_2 \xrightarrow{\text{glucose oxidase}} \text{gluconic acid} + H_2O_2$$

The hydrogen peroxide reacts electrochemically as shown below in equation 2:

$$H_2O_2 \rightarrow 2H^+ + O_2 + 2e^-$$

The current measured by the sensor is generated by the oxidation of the hydrogen peroxide at a platinum working electrode. According to equation 1, if there is excess oxygen for equation 1, then the hydrogen peroxide is stoichiometrically related to the amount of glucose that reacts with the enzyme. In this instance, the ultimate current is also proportional to the amount of glucose that reacts with the enzyme. However, if there is insufficient oxygen for all of the glucose to react with the enzyme, then the current will be proportional to the oxygen concentration, not the glucose concentration. For the glucose sensor to be useful, glucose must be the limiting reagent, i.e., the oxygen concentration must be in excess for all potential glucose concentrations. Unfortunately, this requirement is not easily achieved. For example, in the subcutaneous tissue the concentration of oxygen is much less that of glucose. As a consequence, oxygen can become a limiting reactant, giving rise to a problem with oxygen deficit. Attempts have been made to circumvent this problem in order to allow the sensor to continuously operate in an environment with an excess of oxygen.

Several attempts have been made to use membranes of various types in an effort to control the diffusion of oxygen and glucose to the sensing elements of glucose oxidase-based glucose sensors. One approach has been to develop homogenous membranes having hydrophilic domains dispersed substantially throughout a hydrophobic matrix to circumvent the oxygen deficit problem, where glucose diffusion is facilitated by the hydrophilic segments.

For example, U.S. Pat. No. 5,322,063 to Allen et al. teaches that various compositions of hydrophilic polyurethanes can be used in order to control the ratios of the diffusion coefficients of oxygen to glucose in an implantable glucose sensor. In particular, various polyurethane compositions were synthesized that were capable of absorbing from 10 to 50% of their dry weight of water. The polyurethanes were rendered hydrophilic by incorporating polyethyleneoxide as their soft segment diols. One disadvantage of this invention is that the primary backbone structure of the polyurethane is sufficiently different so that more than one casting solvent may be required to fabricate the membranes. This reduces the ease with which the membranes may be manufactured and may further reduce the reproducibility of the membrane. Furthermore, neither the percent of the polyethyleneoxide soft segment nor the percent water pickup of the polyurethanes disclosed by Allen directly correlate to the oxygen to glucose permeability ratios. Therefore, one skilled in the art cannot simply change the polymer composition and be able to predict the oxygen to glucose permeability ratios. As a result, a large number of polymers would need to be synthesized before a desired specific oxygen to glucose permeability ratio could be obtained.

U.S. Pat. Nos. 5,777,060 and 5,882,494, each to Van Antwerp, also disclose homogeneous membranes having hydrophilic domains dispersed throughout a hydrophobic matrix to reduce the amount of glucose diffusion to the working electrode of a biosensor. For example, U.S. Pat. No. 5,882,494 to Van Antwerp discloses a membrane including the reaction products of a diisocyanate, a hydrophilic diol or diamine, and a silicone material. In addition, U.S. Pat. No. 5,777,060 to Van Antwerp discloses polymeric membranes that can be prepared from (a) a diisocyanate, (b) a hydrophilic polymer, (c) a siloxane polymer having functional groups at the chain termini, and optionally (d) a chain extender. Polymerization of these membranes typically requires heating of the reaction mixture for periods of time from 1 to 4 hours, depending on whether polymerization of the reactants is carried out in bulk or in a solvent system. Therefore, it would be beneficial to provide a method of preparing a homogenous membrane from commercial polymers. Moreover, as mentioned above, one skilled in the art cannot simply change the polymer composition and be able to predict the oxygen to glucose permeability ratios. Therefore, a large number of polymers would need to be synthesized and coating or casting techniques optimized before a desired specific oxygen to glucose permeability ratio could be obtained.

A further membrane is disclosed in U.S. Pat. No. 6,200,772 B1 to Vadgama et al. that has hydrophilic domains dispersed substantially throughout a hydrophobic matrix for limiting the amount of glucose diffusing to a working electrode. In particular, the patent describes a sensor device that includes a membrane comprised of modified polyurethane that is substantially non-porous and incorporates a non-ionic surfactant as a modifier. The non-ionic surfactant is disclosed as preferably including a poly-oxyalkylene chain, such as one derived from multiple units of polyoxyethylene groups. As described, the non-ionic surfactant may be incorporated into the polyurethane by admixture or through compounding to distribute it throughout the polyurethane. The non-ionic surfactant is, according to the specification, preferably incorporated into the polyurethane by allowing it to react chemically with the polyurethane so that it becomes chemically bound into its molecular structure. Like most reactive polymer resins, complete reaction of the surfactant into the polyurethane may never occur. Therefore, a disadvantage of this membrane is that it can leach the surfactant over time and cause irritation at the implant site or change its permeability to glucose.

PCT Application WO 92/13271 discloses an implantable fluid measuring device for determining the presence and the amounts of substances in a biological fluid that includes a membrane for limiting the amount of a substance that passes therethrough. In particular, this application discloses a membrane including a blend of two substantially similar polyurethane urea copolymers, one having a glucose permeability that is somewhat higher than preferred and the other having a glucose permeability that is somewhat lower than preferred.

An important factor in obtaining a useful implantable sensor for detection of glucose or other analytes is the need for optimization of materials and methods in order to obtain predictable in vitro and in vivo function. The ability of the sensor to function in a predictable and reliable manner in vitro is dependent on consistent fabrication techniques. Repeatability of fabrication has been a problem associated with prior art membranes that attempt to regulate the transport of analytes to the sensing elements.

We refer now to FIG. 1, which shows a photomicrograph at 200× magnification of a prior art cast polymer blend following hydration. A disadvantage of the prior art membranes is that, upon thermodynamic separation from the hydrophobic portions, the hydrophilic components form undesirable structures that appear circular 1 and elliptical 2 when viewed with a light microscope when the membrane 3 is hydrated, but not when it is dry. These hydrated structures can be detected by photomicroscopy under magnifications in the range of between 200×-400×, for example. They have been shown by the present inventors to be non-uniform in their dimensions throughout the membrane, with some being of the same size and same order of dimensions as the electrode size. It is believed that these large domains present a problem in that they result in a locally high concentration of either hydrophobic or hydrophilic material in association with the electrode. This can result in glucose diffusion being limited or variable across the dimension adjacent the sensing electrode. Moreover, these large hydrated structures can severely limit the number of glucose diffusion paths available. It is noted that particles 4 in membrane 3 are dust particles.

With reference now to a schematic representation of a known membrane 14 in FIG. 2A, one can consider by way of example a continuous path 16 by which glucose may traverse along the hydrophilic segments 10 that are dispersed in hydrophobic sections 12 of the membrane. For path 16, glucose is able to traverse a fairly continuous path along assembled hydrophilic segments 10 from the side 18 of the membrane in contact with the body fluid containing glucose to the sensing side 20 proximal to sensor 22, where an electrode 24 is placed at position 26 where glucose diffusion occurs adjacent surface 20. In particular, in that portion of the membrane 14 proximal to position 26, glucose diffusion occurs along hydrophilic segments 10 that comprise a hydrated structure 28 having a size and overall dimensions x that are of the same order of magnitude as electrode 24. Therefore, glucose diffusion would be substantially constant across the dimension adjacent electrode 24, but the number of glucose diffusion paths would be limited.

Referring now to FIG. 2B, one can consider an example where glucose traversing prior art membrane 14 from side 18 in contact with the body fluid to the sensing side 20 cannot adequately reach electrode 30. In particular, electrode 30 is located at position 34, which is adjacent to a locally high concentration of a hydrophobic region 12 of prior art membrane 14. In this instance, glucose diffusion cannot adequately occur, or is severely limited across the dimension adjacent the electrode surface. Consequently, one would expect that the locally high concentration of the hydrophobic regions adjacent to working electrode 30 would limit the ability of the sensing device to obtain accurate glucose measurements. The random chance that the membrane could be placed in the 2A configuration as opposed to 2B leads to wide variability in sensor performance.

We also refer to FIG. 2C, which shows another cross-section of prior art membrane 14. In this instance, glucose is able to traverse a fairly continuous path 36 from side 18 to side 20 proximal to the sensing device. However, electrode 38 is located at position 40 such that glucose diffusion is variable across the dimension adjacent the electrical surface. In particular, most of the electrode surface is associated with a locally high concentration of hydrophobic region and a small portion is associated with hydrophilic segments 10 along glucose diffusion path 36. Furthermore, glucose diffusing along path 36a would not be associated with the electrode. Again, the large non-uniform structures of the prior art membranes can limit the number of glucose diffusion paths and the ability of the sensing device to obtain accurate glucose measurements.

It would be beneficial to form more homogeneous membranes for controlling glucose transport from commercially available polymers that have a similar backbone structure. This would result in a more reproducible membrane. In particular, it is desired that one would be able to predict the resulting glucose permeability of the resulting membrane by simply varying the polymer composition. In this way, the glucose diffusion characteristics of the membrane could be modified, without greatly changing the manufacturing parameters for the membrane. In particular, there is a need for homogeneous membranes having hydrophilic segments dispersed throughout a hydrophobic matrix that are easy to fabricate reproducibly from readily available reagents. Of particular importance would be the development of membranes where the hydrophilic portions were distributed evenly throughout the membrane, and where their size and dimensions were on an order considerably less than the size and dimensions of the electrode of the sensing device to allow the electrode to be in association with a useful amount of both hydrophobic and hydrophilic portions. The ability of the membranes to be synthesized and manufactured in reasonable quantities and at reasonable prices would be a further advantage.

SUMMARY OF THE INVENTION

The present invention provides an implantable membrane for controlling the diffusion of an analyte therethrough to a biosensor with which it is associated. In particular, the membrane of the present invention satisfies a need in the art by providing a homogenous membrane with both hydrophilic and hydrophobic regions to control the diffusion of glucose and oxygen to a biosensor, the membrane being fabricated easily and reproducibly from commercially available materials.

The invention provides a biocompatible membrane that regulates the transport of analytes that includes: (a) a matrix including a first polymer; and (b) a second polymer dispersed throughout the matrix, wherein the second polymer forms a network of microdomains which when hydrated are not observable using photomicroscopy at 400× magnification or less.

Further provided by the invention is a polymeric membrane for regulation of glucose and oxygen in a subcutaneous glucose measuring device that includes: (a) a matrix including a first polymer; and (b) a second polymer dispersed throughout the matrix, wherein the second polymer forms a network of microdomains which are not photomicroscopically observable when hydrated at 400× magnification or less.

Yet another aspect of the present invention is directed to a polymeric membrane for regulating the transport of analytes, the membrane including at least one block copolymer AB, wherein B forms a network of microdomains which are not photomicroscopically observable when hydrated at 400× magnification or less.

Also provided is a membrane and sensor combination, the sensor being adapted for evaluating an analyte within a body fluid, the membrane having: (a) a matrix including a first polymer; and (b) a second polymer dispersed throughout the matrix, wherein the second polymer forms a network of microdomains which are not photomicroscopically observable when hydrated at 400× magnification or less.

The invention further provides an implantable device for measuring an analyte in a hydrophilic body fluid, including: (a) a polymeric membrane having (i) a matrix including a first polymer; and (ii) a second polymer dispersed throughout the matrix, wherein the second polymer forms a network of microdomains which are not photomicroscopically observable when hydrated at 400× magnification or less; and (b) a proximal layer of enzyme reactive with the analyte.

Moreover, a method for preparing an implantable membrane according to the invention is provided, the method including the steps of: (a) forming a composition including a dispersion of a second polymer within a matrix of a first polymer, the dispersion forming a network of microdomains which are not photomicroscopically observable when hydrated at 400× magnification or less; (b) maintaining the composition at a temperature sufficient to maintain the first polymer and the second polymer substantially soluble; (c) applying the composition at this temperature to a substrate to form a film thereon; and (d) permitting the resultant film to dry to form the membrane.

DETAILED WRITTEN DESCRIPTION

In order to facilitate understanding of the present invention, a number of terms are defined below.

The term "analyte" refers to a substance or chemical constituent in a biological fluid (e.g. blood or urine) that is intended to be analyzed. A preferred analyte for measurement by analyte detecting devices including the membrane of the present invention is glucose.

The term "sensor" refers to the component or region of a device by which an analyte can be evaluated.

By the terms "evaluated", "monitored", "analyzed", and the like, it is meant that an analyte may be detected and/or measured.

The phrase "continuous glucose sensing" refers to the period in which monitoring of plasma glucose concentration is repeatedly performed over short periods of time, for example, 10 seconds to about every 15 minutes.

The term "domain" refers to regions of the membrane of the present invention that may be layers, uniform or non-uniform gradients (e.g. anisotropic) or provided as portions of the membrane. Furthermore, the region possesses physical properties distinctly different from other portions of the membrane.

The terms "accurate" and "accurately" means, for example, 85% of measured glucose values are within the "A" and "B" region of a standard Clarke Error Grid when the sensor measurements are compared to a standard reference measurement. It is understood that like any analytical device, calibration, calibration validation and recalibration are required for the most accurate operation of the device.

The term "host" refers to humans and other animals.

In the disclosure that follows, the invention will primarily be referred to in terms of assay of glucose and solutions such as blood that tend to contain a large excess of glucose over oxygen. However, it is well within the contemplation of the present invention that the membrane is not limited solely to the assay of glucose in a biological fluid, but may be used for the assay of other compounds. In addition, the sensor primarily referred to is an electrochemical sensor that directly measures hydrogen peroxide. However, it is well within the contemplation of the present invention that nonelectrochemical based sensors that use optical detectors or other suitable detectors may be used to evaluate an analyte.

Membranes of the prior art have generally been unreliable at limiting the passage of glucose to implantable glucose sensors. This has presented a problem in the past in that the amount of glucose coming into contact with the immobilized enzyme exceeds the amount of oxygen available. As a result, the oxygen concentration is the rate-limiting component of the reaction, rather than the glucose concentration, such that the accuracy of the glucose measurement in the body fluid is compromised.

Figure 1:
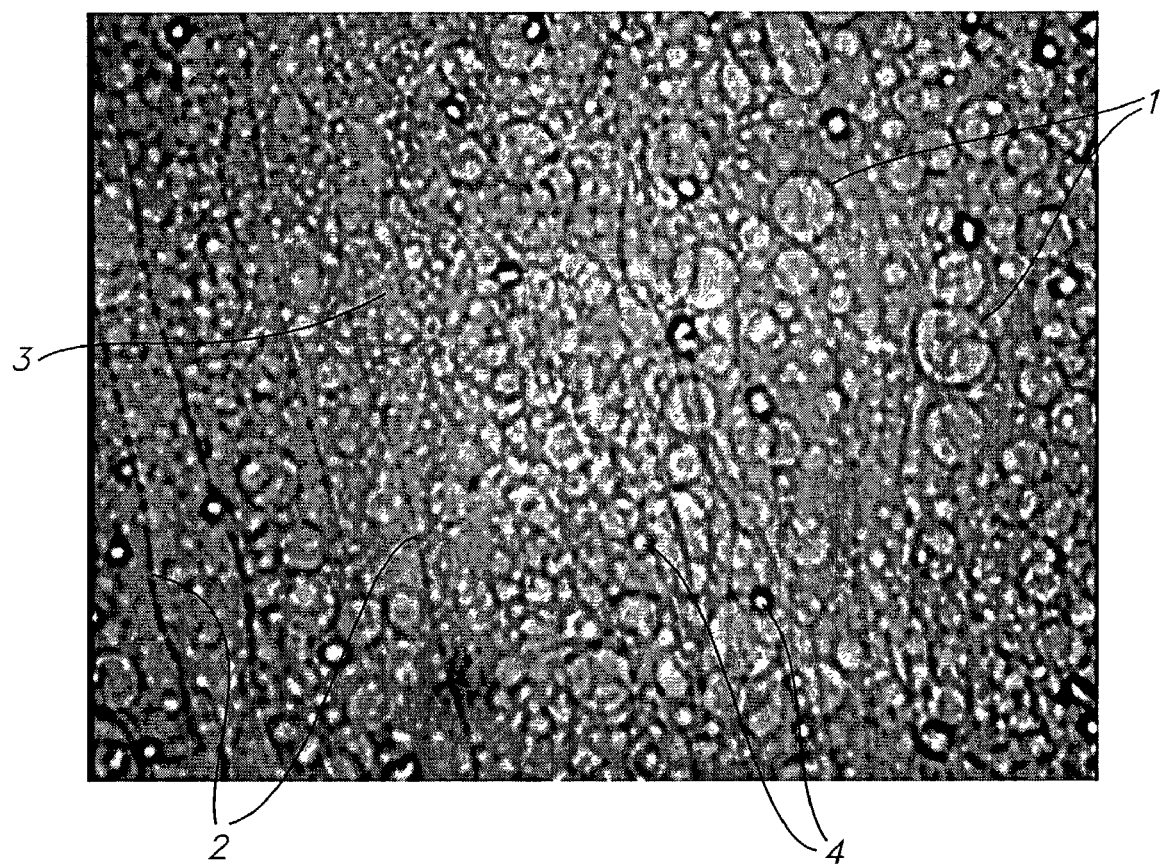
FIG. 1 is a photomicrograph of a cross-section of prior art membrane at 200× magnification following hydration with water for two hours.
Figure 2A:
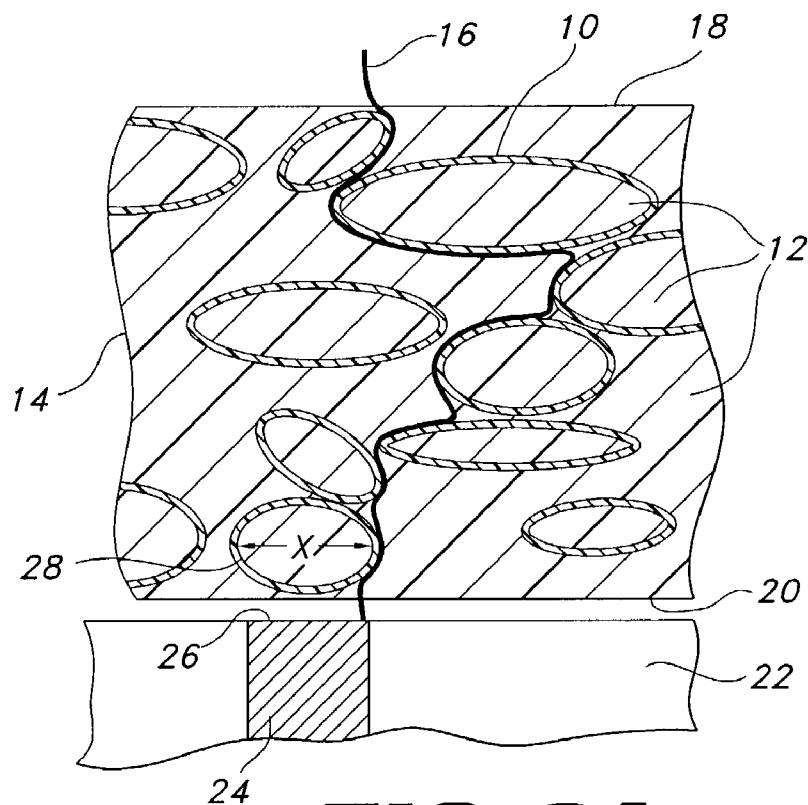
FIG. 2A is a schematic representation of a cross-section of a prior art membrane having large hydrated structures dispersed substantially throughout a hydrophobic matrix, the hydrated structures being photomicroscopically observable at 400× magnification or less. The figure illustrates the positioning of a working electrode relative to a glucose diffusion pathway.
Figure 2B:
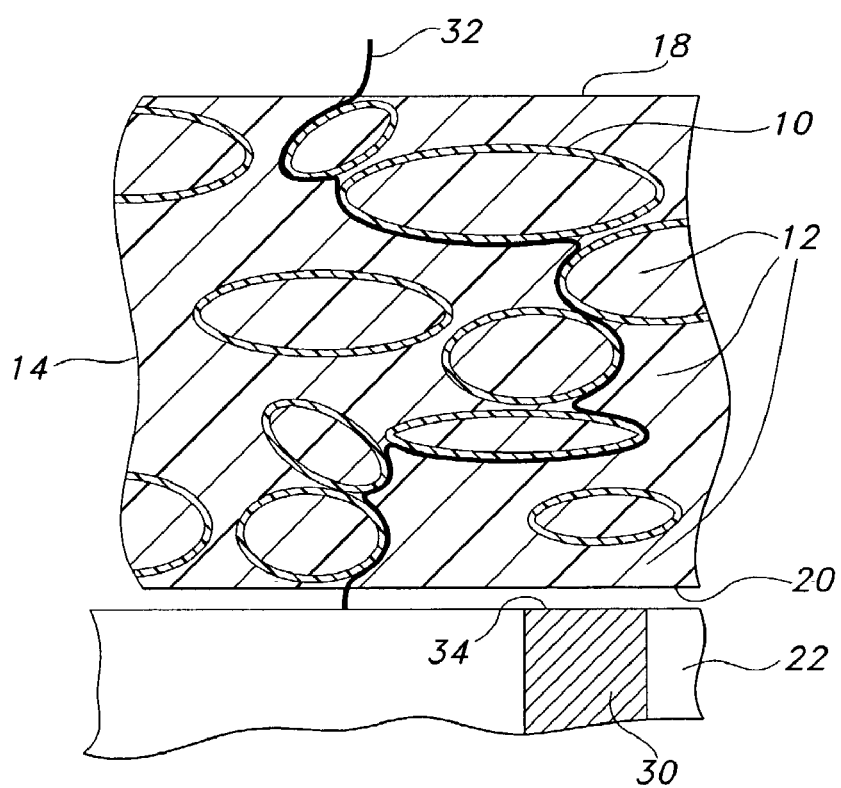
FIG. 2B is another schematic representation of a cross-section of the prior art membrane of FIG. 2A, where the working electrode is placed in association with a locally high concentration of the hydrophobic matrix.
Figure 2C:
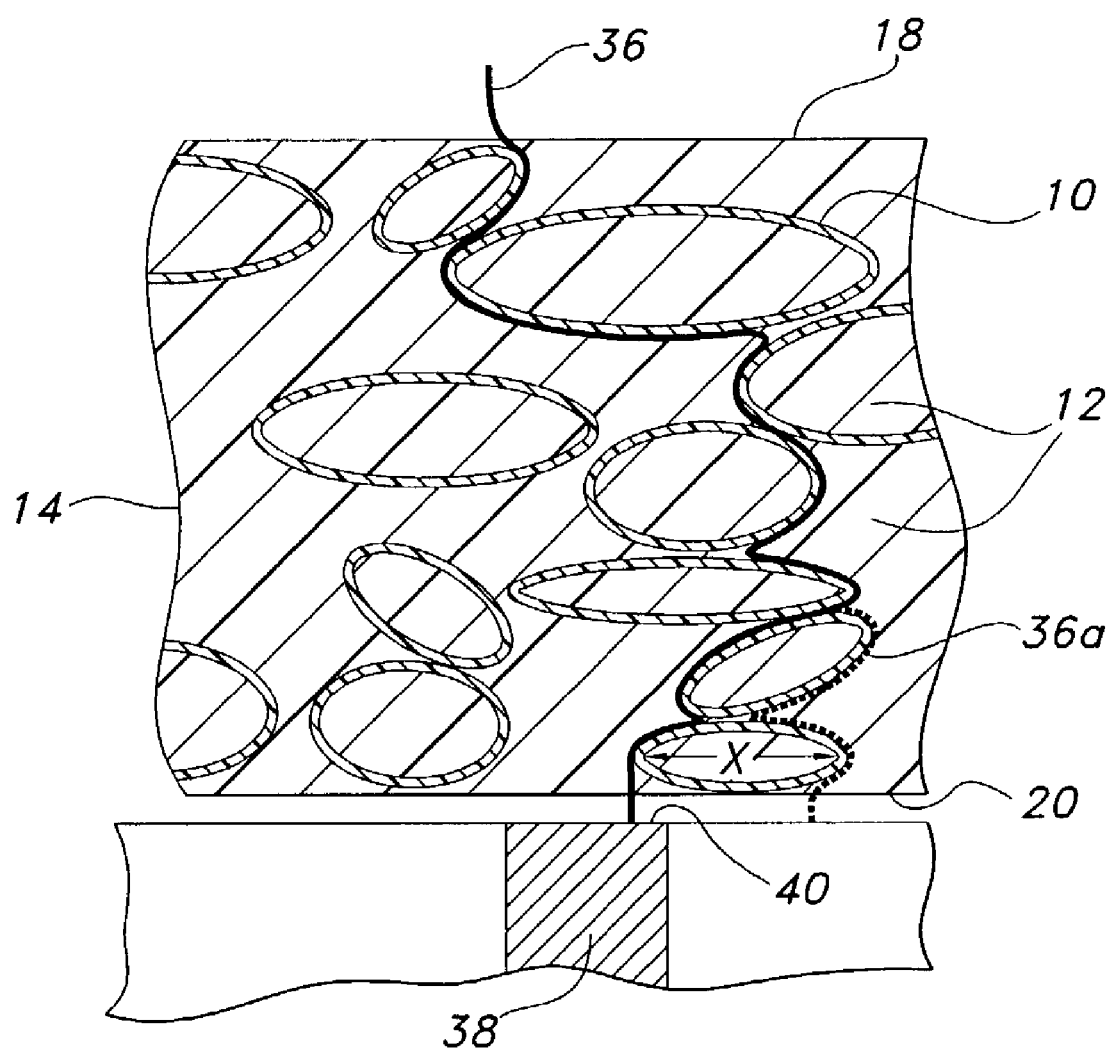
FIG. 2C is yet another schematic representation of a cross-section of the prior art membrane of FIG. 2A where glucose diffusion is variable across the dimension adjacent the electrode surface.

As described above, in contrast to the present invention, a disadvantage of prior art membranes for regulating analyte transport therethrough has been their tendency to form large undesirable structures (see FIG. 1) that are observable when the membrane is hydrated. In particular, these hydrated structures can be detected by photomicroscopy under magnifications in the range of between 200×-400×, for example. They have been shown by the present inventors to be non-uniform in their dimensions through the membrane, with some being of the same size and same order of dimensions as the electrode size. These large structures have been found to be problematic in that they can result in a locally high concentration of either hydrophobic or hydrophilic material in association with the working electrode, which can lead to inaccurate glucose readings. Moreover, they can greatly reduce the number of glucose diffusion paths available.

The membrane of the present invention seeks to circumvent these problems associated with prior art membranes by providing a reliable homogeneous membrane that regulates the transport of glucose or other analytes therethrough, the membrane having (a) a matrix including a first polymer; and (b) a second polymer dispersed throughout the matrix, wherein the second polymer forms a network of microdomains which when hydrated are not observable using photomicroscopy at 400× magnification or less. In one embodiment of the invention, the membrane is substantially free of observable domains.

Figure 3:
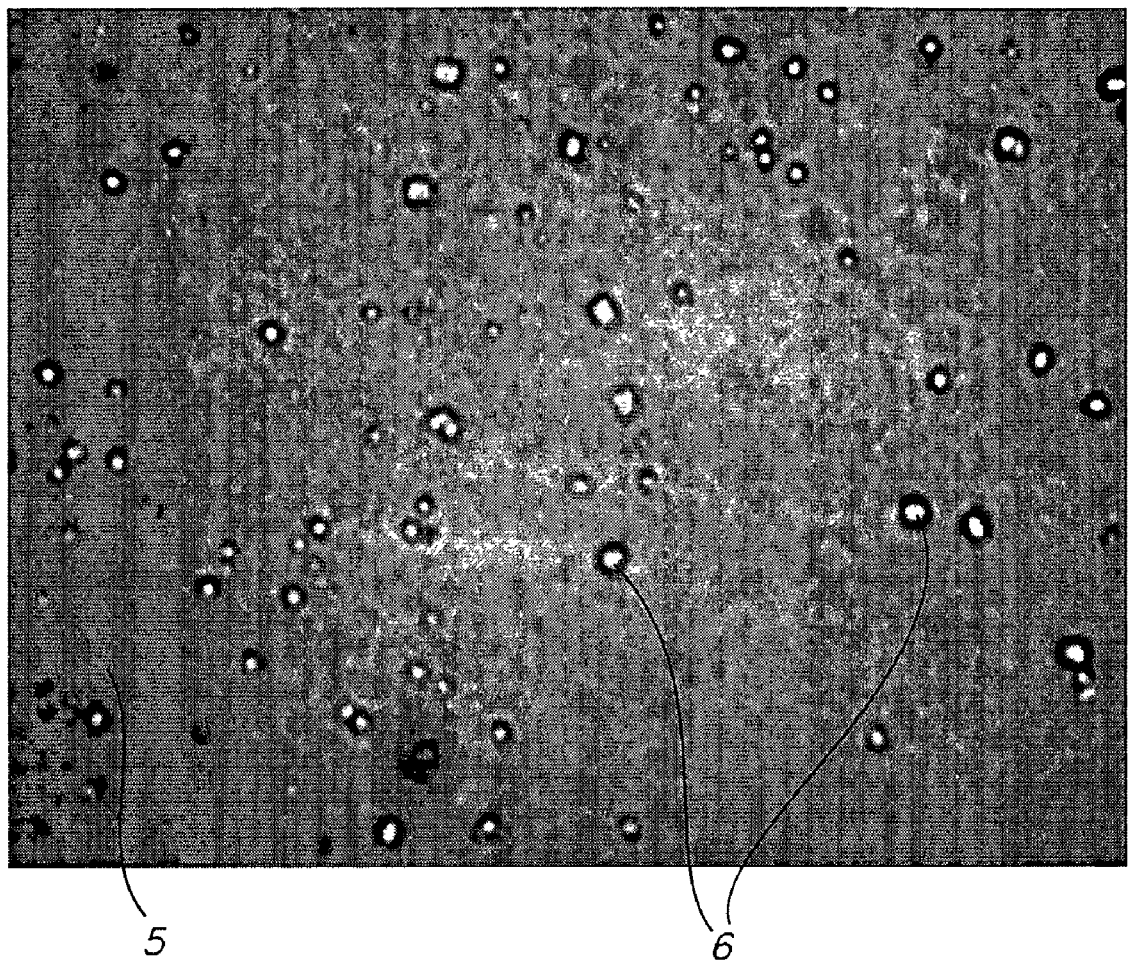
FIG. 3 is a photomicrograph of a cross-section of a membrane of the present invention at 200× magnification following hydration with water for two hours.

We refer now to FIG. 3, which shows a photomicrograph of a cross-section of a membrane 5 according to the present invention following hydration at two hours. As shown in FIG. 3, the membrane is devoid of any undesirable, large elliptical or spherical structures, such as were observable in hydrated prior art membranes at similar magnifications. It is noted that particles 6 in membrane 5 are dust particles.

For purposes of the present invention, it is likely that glucose permeability and diffusion is related to the ratio of hydrophobic to hydrophilic constituents and their distribution throughout the membrane, with diffusion occurring substantially along assembled hydrophilic segments from the side of the membrane in contact with the host to the sensing side.

Figure 4:
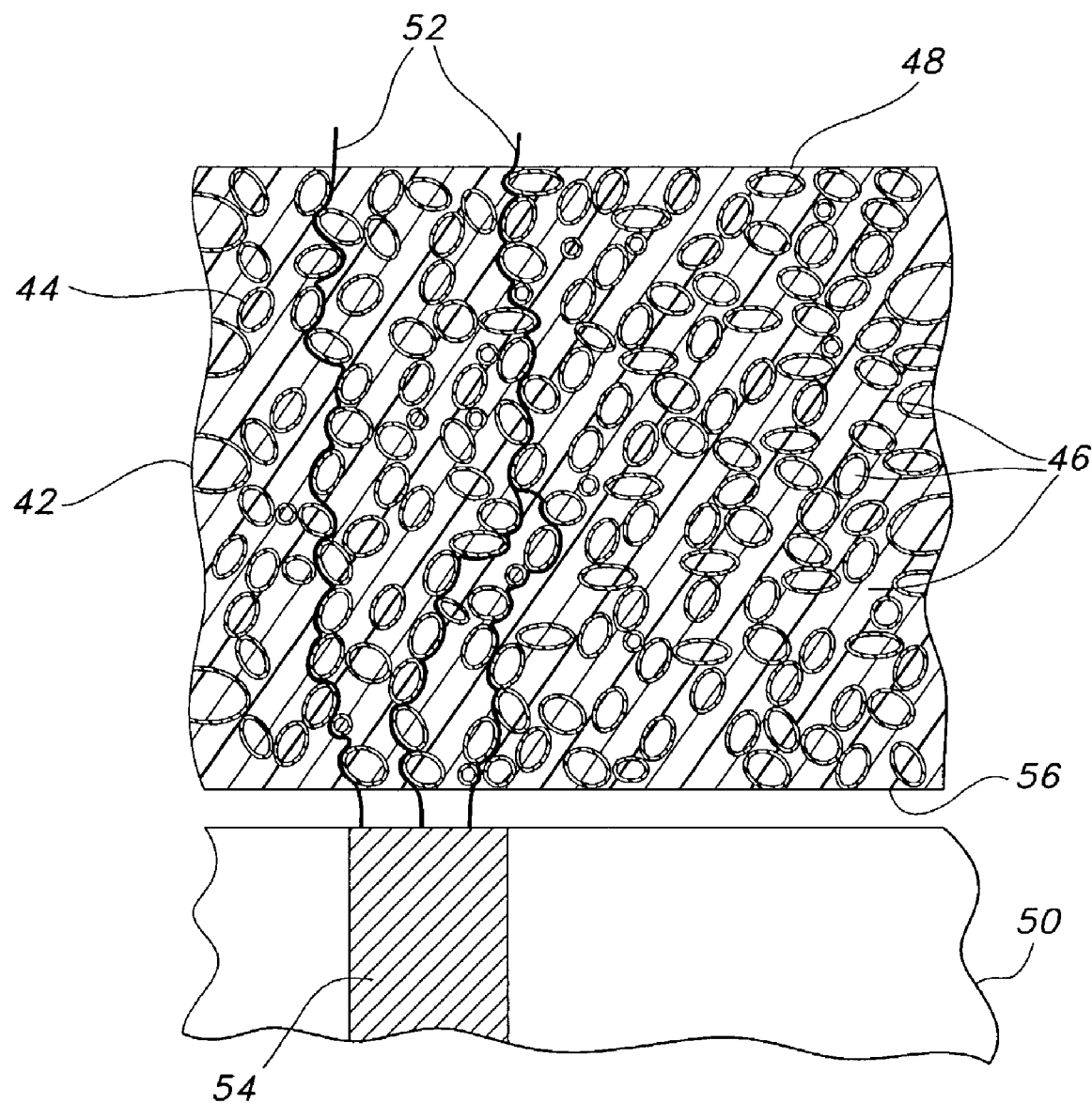
FIG. 4 is a schematic representation of a cross-section illustrating one particular form of the membrane of the present invention that shows a network of microdomains which are not photomicroscopically observable at 400× or less magnification dispersed through a hydrophobic matrix, where the membrane is positioned in association with a sensor that includes a working electrode.

Referring now to FIG. 4, membrane 42 of the present invention, in accordance with a particular arrangement, is schematically shown having hydrophilic segments 44 dispersed substantially throughout a hydrophobic matrix 46 and presenting a surface 48 to a hydrophilic body fluid. The hydrophilic body fluid contains the sample to be assayed. In one embodiment, the body fluid contains both glucose and oxygen. Membrane 42 restricts the rate at which glucose enters and passes through the membrane and/or may increase the rate at which oxygen enters and passes through membrane 42.

While not wishing to be bound by any one theory, it is likely that glucose diffuses substantially along hydrophilic segments 44, but is generally excluded from the hydrophobic matrix 46. It is noted that while the hydrophilic segments 44 are shown as comprising discrete microdomains in FIG. 4, small amounts of hydrophobic polymer may be present therein, particularly at the interface with the hydrophobic matrix 46. Similarly, small amounts of hydrophilic polymer may be present in the hydrophobic matrix 46, particularly at the interface with hydrophilic segments 44.

In the embodiment shown in FIG. 4, inventive membrane 42 is shown in combination with a sensor 50, which is positioned adjacent to the membrane. It is noted that additional membranes or layers may be situated between membrane 42 and sensor 50, as will be discussed in further detail below. Diffusion of the sample along paths 52 through membrane 42 into association with a working electrode 54 of sensor 50 causes development of a signal that is proportional to the amount of analyte in the sample. Determination of the analyte may be made by calculations based upon similar measurements made on standard solutions containing known concentrations of the analyte. For example, one or more electrodes may be used to detect the amount of analyte in the sample and convert that information into a signal; the signal may then be transmitted to electronic circuitry required to process biological information obtained from the host. U.S. Pat. Nos. 4,757,022, 5,497,772 and 4,787,398 describe suitable electronic circuitry that may be utilized with implantable devices of the present invention.

The present invention solves a need in the art by providing a reliable membrane for controlling glucose diffusion therethrough. As shown in FIG. 4, glucose can traverse along hydrophilic segments 44 from the side 48 of the membrane in contact with a body fluid to the side 56 proximal to sensor 50. The hydrophilic microdomains 44 are likely distributed substantially evenly throughout the membrane. Furthermore, these microdomains are likely substantially uniform in size throughout the membrane. The size and order to dimensions of these microdomains is considerably less than the that of the working electrode 54 of sensor 50. As such, the electrode is in association with a useful amount of both the hydrophobic 46 and hydrophilic 44 regions of the membrane to allow effective control over the amount of glucose diffusing to the electrode. Moreover, as shown in FIG. 4, the number of paths available for glucose to permeate the membrane and diffuse from side 48 to the sensing side 56 would be greater for the inventive membrane than for prior art membranes. Consequently, more accurate and reproducible glucose readings are attainable across the entire inventive membrane.

Figure 5:
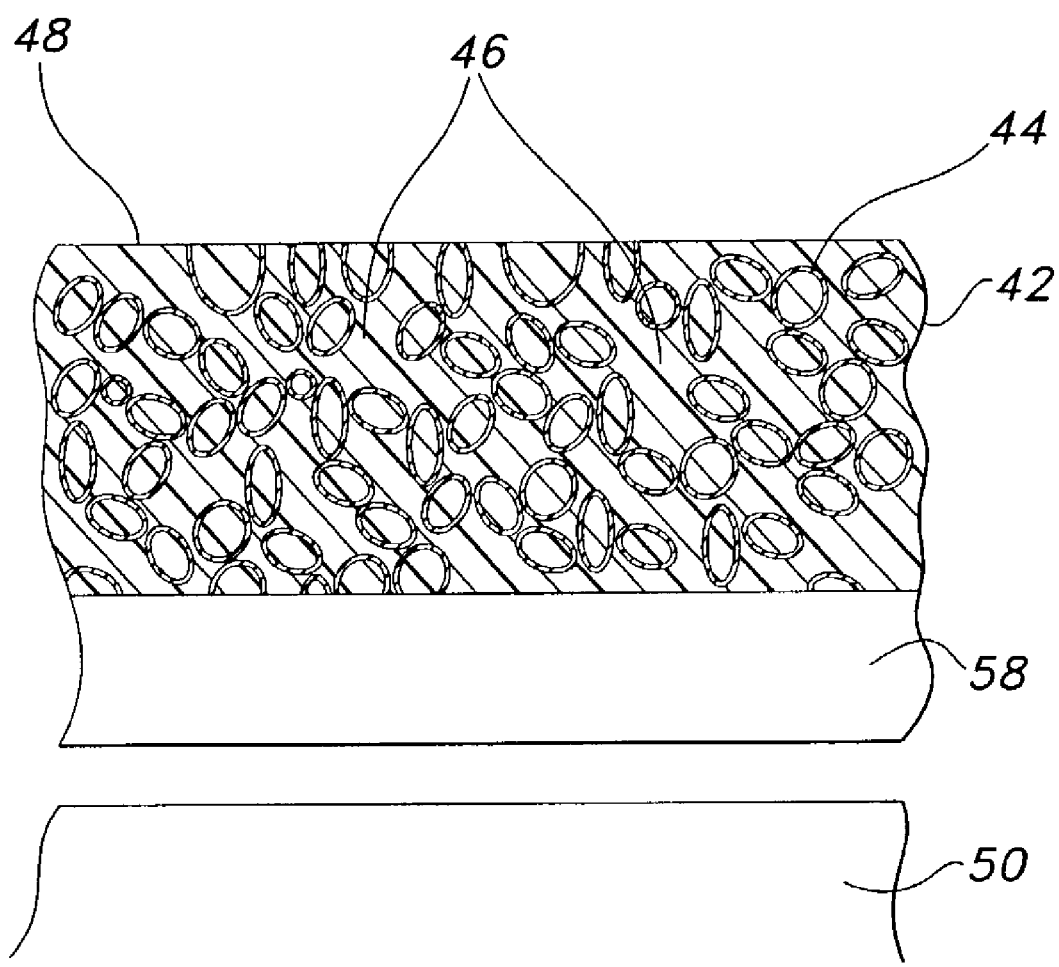
FIG. 5 is a schematic representation of a cross-section of the membrane of FIG. 3 in combination with an enzyme containing layer positioned more adjacent to a sensor 50.

FIG. 5 shows a preferred embodiment of the present invention wherein membrane 42 is used in combination with a proximal membrane layer 58 that comprises an enzyme that is reactive with the analyte. In this instance, diffusion of the sample from side 48 through the membrane 42 into contact with the immobilized enzyme in layer 58 leads to an enzymatic reaction in which the reaction products may be measured. For example, in one embodiment the analyte is glucose. In a further embodiment, the enzyme immobilized in layer 58 is glucose oxidase.

As described above, glucose oxidase catalyzes the conversion of oxygen and glucose to hydrogen peroxide and gluconic acid. Because for each glucose molecule metabolized, there is proportional change in the co-reactant $O_2$ and the product $H_2O_2$, one can monitor the change in either the co-reactant or the product to determine glucose concentration. With further reference to FIG. 5, diffusion of the resulting hydrogen peroxide through layer 58 to the sensor 50, (e.g. electrochemically reactive surfaces), causes the development of an electrical current that can be detected.

This enables determination of the glucose by calculations based upon similar measurements made on standard solutions containing known concentrations of glucose.

In addition to glucose oxidase, the present invention contemplates the use of a layer impregnated with other oxidases, e.g. galactose oxidase or uricase. For an enzyme-based electrochemical glucose sensor to perform well, the sensor's response must neither be limited by enzyme activity nor cofactor concentration. Because enzymes, including glucose oxidase, are subject to deactivation as a function of ambient conditions, this behavior needs to be accounted for in constructing sensors for long-term use.

When the membrane of the present invention is combined with an enzyme layer 58 as shown in FIG. 5, it is the enzyme layer that is located more proximally to the sensor 50 (e.g. electrochemically reactive surfaces). It is noted that enzyme-containing layer 58 must be of sufficient permeability to 1) freely pass glucose to active enzyme and 2) to permit the rapid passage of hydrogen peroxide to the sensor (electrode surface). A failure to permit the rapid passage of glucose to the active enzyme or hydrogen peroxide from the active enzyme to the electrode surface can cause a time delay in the measured signal and thereby lead to inaccurate results.

Preferably, the enzyme layer is comprised of aqueous polyurethane-based latex into which the enzyme is immobilized.

It is noted that while the inventive membrane 42 may itself contain immobilized enzymes for promoting a reaction between glucose and oxygen, it is preferred that the enzyme be located in a separate layer, such as layer 58 shown in FIG. 5. As described above, it is known that enzyme actively reacting with glucose is more susceptible to irreversible inactivation. Therefore, a disadvantage of providing enzyme in a layer that is semi-permeable to glucose, is that the calibration factors of the sensor may change over time as the working enzyme degrades. In contrast, when enzyme is dispersed throughout a membrane freely permeable to glucose (i.e. layer 58 in FIG. 5), such a membrane is likely to yield calibration factors that are more stable over the life of a sensor.

In one preferred embodiment of the invention, the first polymer of the membrane includes homopolymer A and the second polymer includes copolymer AB.

In another embodiment, the first polymer includes copolymer AB and the second polymer includes copolymer AB. Preferably, the amount of B in copolymer AB of the first polymer is different than the amount of B in copolymer AB of the second polymer. In particular, the membrane may be formed from a blend of two AB copolymers, where one of the copolymers contains more of a hydrophilic B polymer component than the blended targeted amount and the other copolymer contains less of a hydrophilic B polymer component than the blended targeted amount.

In yet another embodiment of the invention, the first polymer includes homopolymer A and the second polymer includes homopolymer B.

As described above, the invention also provides a polymeric membrane for regulating the transport of analytes that includes at least one block copolymer AB, wherein B forms a network of microdomains which are not photomicroscopically observable when hydrated at 400× magnification or less. In one embodiment, the ratio of A to B in copolymer AB is 70:30 to 90:10.

For each of the inventive embodiments herein described, homopolymer A is preferably a hydrophobic A polymer. Moreover, copolymer AB is preferably a hydrophobic-hydrophilic copolymer component that includes the reaction products of a hydrophobic A polymer and a hydrophilic B polymer. Suitable materials for preparing membranes the present invention are described below.

For purposes of the present invention, copolymer AB may be a random or ordered block copolymer. Specifically, the random or ordered block copolymer may be selected from the following: ABA block copolymer, BAB block copolymer, AB random alternating block copolymer, AB regularly alternating block copolymer and combinations thereof.

In a preferred embodiment, the sensor, membrane, and methods of the present invention may be used to determine the level of glucose or other analytes in a host. The level of glucose is a particularly important measurement for individuals having diabetes in that effective treatment depends on the accuracy of this measurement.

In particular, the invention provides a method of measuring glucose in a biological fluid that includes the steps of: (a) providing (i) a host, and (ii) an implantable device for measuring an analyte in a hydrophilic body fluid, where the device includes a polymeric membrane having a matrix including a first polymer and a second polymer dispersed throughout the matrix, wherein the second polymer forms a network of microdomains which are not photomicroscopically observable when hydrated at 400× magnification or less; and a proximal layer of enzyme reactive with the analyte; and (b) implanting the device in the host. In one embodiment, the device is implanted subcutaneously.

The invention also provides a method of measuring glucose in a biological fluid that includes the following steps: (a) providing (i) a host, and (ii) an implantable device for measuring an analyte in a hydrophilic body fluid, that includes a polymeric membrane including a matrix including a first polymer and a second polymer dispersed throughout the matrix, wherein the second polymer forms a network of microdomains which are not photomicroscopically observable when hydrated at 400× magnification or less; and a proximal layer of enzyme reactive with the analyte, the device being capable of accurate continuous glucose sensing; and (b) implanting the device in the host. Desirably, the implant is placed subcutaneously in the host.

Glucose sensors that use, for example, glucose oxidase to effect a reaction of glucose and oxygen are known in the art, and are within the skill of one in the art to fabricate (see, for example, U.S. Pat. Nos. 5,165,407, 4,890,620, 5,390,671, 5,391,250, 6,001,067 as well as copending, commonly owned U.S. patent application Ser. No. 09/916,858. It is noted that the present invention does not depend on a particular configuration of the sensor, but is rather dependent on the use of the inventive membrane to cover or encapsulate the sensor elements.

For the electrochemical glucose sensor to provide useful results, the glucose concentration, as opposed to oxygen concentration, must be the limiting factor. In order to make the system sensitive to glucose concentration, oxygen must be present within the membrane in excess of the glucose. In addition, the oxygen must be in sufficient excess so that it is also available for electrochemical reactions occurring at the amperometric electrode surfaces. In a preferred embodiment, the inventive membrane is designed so that oxygen can pass readily into and through the membrane and so that a reduced amount of glucose diffuses into and through the membrane into contact with an immobilized glucose oxidase enzyme. The inventive membrane allows the ratio of oxygen to glucose to be changed from a concentration ratio in the body fluid of about approximately 50 and 100 parts of glucose to 1 of oxygen to a new ratio in which there is a stoichiometric excess of oxygen in the enzyme layer.

Through the use of the inventive membrane, an implantable glucose sensor system is not limited by the concentration of oxygen present in subcutaneous tissues and can therefore operate under the premise that the glucose oxidase reaction behaves as a 1-substrate (glucose) dependent process.

The present invention provides a semi-permeable membrane that controls the flux of oxygen and glucose to an underlying enzyme layer, rendering the necessary supply of oxygen in non-rate-limiting excess. As a result, the upper limit of linearity of glucose measurement is extended to a much higher value than that which could be achieved without the membrane of the present invention. In particular, in one embodiment the membrane of the present invention is a polymer membrane with oxygen-to-glucose permeability ratios of approximately 200:1; as a result, 1-dimensional reactant diffusion is adequate to provide excess oxygen at all reasonable glucose and oxygen concentrations found in a subcutaneous matrix [Rhodes, et al., Anal. Chem., 66: 1520-1529 (1994)].

A hydrophilic or "water loving" solute such as glucose is readily partitioned into a hydrophilic material, but is generally excluded from a hydrophobic material. However, oxygen can be soluble in both hydrophilic and hydrophobic materials. These factors affect entry and transport of components in the inventive membrane. The hydrophobic portions of the inventive membrane hinder the rate of entry of glucose into the membrane, and therefore to the proximal enzyme layer while providing access of oxygen through both the hydrophilic and hydrophobic portions to the underlying enzyme.

In one preferred embodiment, the membrane of the invention is formed from a blend of polymers including (i) a hydrophobic A polymer component; and (ii) a hydrophobic-hydrophilic copolymer component blended with component (i) that forms hydrophilic B domains that control the diffusion of an analyte therethrough, wherein the copolymer component includes a random or ordered block copolymer. Suitable block copolymers are described above. One is able to modify the glucose permeability and the glucose diffusion characteristics of the membrane by simply varying the polymer composition.

In one preferred embodiment, the hydrophobic A polymer is a polyurethane. In a most preferred embodiment, the polyurethane is polyetherurethaneurea. A polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from 4 to 8 methylene units. Diisocyanates containing cycloaliphatic moieties, may also be useful in the preparation of the polymer and copolymer components of the membrane of the present invention. The invention is not limited to the use of polyurethanes as the hydrophobic polymer A component. The material that forms the basis of the hydrophobic matrix of the inventive membrane may be any of those known in the art as appropriate for use as membranes in sensor devices and having sufficient permeability to allow relevant compounds to pass through it, for example, to allow an oxygen molecule to pass through the inventive membrane from the sample under examination in order to reach the active enzyme or electrochemical electrodes. Examples of materials which may be used to make a non-polyurethane type membrane include vinyl polymers, polyethers, polyesters, polyamides, inorganic polymers such as polysiloxanes and polycarbosiloxanes, natural polymers such as cellulosic and protein based materials and mixtures or combinations thereof.

As described above, the hydrophobic-hydrophilic copolymer component includes the reaction products of a hydrophobic A polymer component and a hydrophilic B polymer component. The hydrophilic B polymer component is desirably polyethylene oxide. For example, one useful hydrophobic-hydrophilic copolymer component is a polyurethane polymer that includes about 20% hydrophilic polyethyelene oxide. The polyethylene oxide portion of the copolymer is thermodynamically driven to separate from the hydrophobic portions of the copolymer and the hydrophobic A polymer component. The 20% polyethylene oxide based soft segment portion of the copolymer used to form the final blend controls the water pick-up and subsequent glucose permeability of the membrane of the present invention.

The polyethylene oxide may have an average molecular weight of from 200 to 3000 with a preferred molecular weight range of 600 to 1500 and preferably constitutes about 20% by weight of the copolymer component used to form the membrane of the present invention.

It is desired that the membrane of the present invention have a thickness of about 5 to about 100 microns. In preferred embodiments, the membrane of the present invention is constructed of a polyetherurethaneurea/polyetherurethaneurea-block-polyethylene glycol blend and has a thickness of not more than about 100 microns, more preferably not less than about 10 microns, and not more than about 80 microns, and most preferably, not less than about 20 microns, and not more than about 60 microns.

The membrane of the present invention can be made by casting from solutions, optionally with inclusion of additives to modify the properties and the resulting cast film or to facilitate the casting process.

The present invention provides a method for preparing the implantable membrane of the invention. The method includes the steps of: (a) forming a composition including a dispersion of a second polymer within a matrix of a first polymer, the dispersion forming a network of microdomains which are not photomicroscopically observable when hydrated at 400× magnification or less; (b) maintaining the composition at a temperature sufficient to maintain the first polymer and the second polymer substantially soluble; (c) applying the composition at the temperature to a substrate to form a film thereon; and (d) permitting the resultant film to dry to form the membrane. In one embodiment, the forming step includes forming a mixture or a blend. As described above, in preferred embodiments, the first polymer is a polyurethane and the second polymer is polyethylene oxide. In general, the second polymer may be a random or ordered block copolymer selected from the following: ABA block copolymer, BAB block copolymer, AB random alternating block copolymer, AB regularly alternating block copolymer and combinations thereof.

In one embodiment, the composition comprised of a dispersion of the second polymer within the matrix of a first polymer is heated to a temperature of about 70° C. to maintain the first and second polymers substantially soluble. For example, the combination of a hydrophobic polymer A component and a hydrophobic-hydrophilic copolymer AB component is desirably exposed to a temperature of about 70° C. to maintain the polymer and copolymers substantially soluble. In particular, the blend is heated well above room temperature in order to keep the hydrophilic and hydrophobic components soluble with each other and the solvent.

The invention contemplates permitting the coated film formed on the substrate to dry at a temperature from about 120° C. to about 150° C. The elevated temperature further serves to drive the solvent from the coating as quickly as possible. This inhibits the hydrophilic and hydrophobic portions of the membrane from segregating and forming large undesired structures.

The membrane and sensor combinations of the present invention provide a significant advantage over the prior art in that they provide accurate sensor operation at temperatures from about 30° C. to about 45° C. for a period of time exceeding about 30 days to exceeding about a year.

EXAMPLES

Example 1

A Method for Preparing a Membrane of the Present Invention

The inventive membrane may be cast from a coating solution. The coating solution is prepared by placing approximately 281 gm of dimethylacetamide (DMAC) into a 3 L stainless steel bowl to which a solution of polyetherurethaneurea (344 gm of Chronothane H (Cardiotech International, Inc., Woburn, Mass.), 29,750 cp @ 25% solids in DMAC) is added. To this mixture is added another polyetherurethaneurea (approximately 312 gm, Chronothane 1020 (Cardiotech International, Inc., Woburn, Mass.), 6275 cp @ 25% solids in DMAC). The bowl is then fitted to a planetary mixer with a paddle-type blade and the contents are stirred for 30 minutes at room temperature. Coatings solutions prepared in this manner are then coated at between room temperature to about 70° C. onto a PET release liner (Douglas Hansen Co., Inc., Minneapolis, Minn.) using a knife-over-roll set at a 0.012 inch gap. The film is continuously dried at 120° C. to about 150° C. The final film thickness is approximately 0.0015 inches.

An Optical Method for Evaluating a Membrane of the Present Invention

A ¼" by ¼" piece of membrane is first immersed in deionized water for a minimum of 2 hours at room temperature. After this time, the sample is placed onto a microscope slide along with one drop of water. A glass cover slide is then placed over the membrane and gentle pressure is applied in order to remove excess liquid from underneath the cover glass. In this way, the membrane does not dry during its evaluation. The hydrated membrane sample is first observed at 40×-magnification using a light microscope (Nikon Eclipse E400). If air bubbles are present on the top or bottom of the film, the cover glass is gently pressed again with a tissue in order to remove them. Magnification is then increased to 200×; and the hydrated membrane is continuously observed while changing the focus from the top to bottom of the film. This is followed by an increase in magnification to 400×, with the membrane again being continuously observed while changing the focus from the top to bottom of the film.

Results

Based on the results of an optical micrograph of a sample membrane prepared by using a room temperature coating solution and drying of the coated film at 120° C., the micrograph being captured as described above, it was noticed that both circular and elliptical domains were present throughout the hydrated section of membrane. At the same magnification, the domains were not observable in dry membrane. Giving that in an electrochemical sensor, the electrodes included therein are typically of the same size and same order of dimensions as the observed circular and elliptical domains, such domains are not desired. These domains present a problem in that they result in a locally high concentration of either hydrophilic or hydrophobic material in association with the electrodes.

Example 2

Optimizing the Coating Solution Conditions

This example demonstrates that preheating the coating solution to a temperature of 70° C. prior to coating eliminates the presence of both the circular and elliptical domains that were present throughout the hydrated cross-section of a membrane prepared using a room temperature coating solution and drying of the coated film at 120° C. Example 2 further demonstrates that, provided the coating solution is preheated to about 70° C., either a standard (120°) or elevated (150° C.) drying temperature were sufficient to drive the DMAC solvent from the coated film quickly to further inhibit the hydrophilic and hydrophobic portions of the polyurethane membrane from segregating into large domains.

In particular, the invention was evaluated by performing a coating experiment where standard coating conditions (room temperature coating solution and 120° C. drying temperature of the coated film) were compared to conditions where the coating solution temperature was elevated and/or the drying temperature of the coated film was elevated. Four experimental conditions were run as follows:

SS-room temperature solution and standard (120° C.) oven temperature.
SE-room temperature solution and elevated (150° C.) oven temperature.
ES-preheated (70° C.) solution and standard (120° C.) oven temperature.
EE-preheated (70° C.) solution and elevated (150° C.) oven temperature.

Results

Samples of each of the four membranes listed above were then hydrated for 2 hours, and then observed under the microscope. Performance specifications were achieved when the micrograph of the membrane prepared under a given condition showed an absence of circular and/or elliptical domains that result in an undesirable, discontinuous hydrophilic and hydrophobic membrane structure. Table 1 below summarizes these results where (+) indicates a membrane meeting desired performance specifications and (−) is indicative of a membrane showing the undesirable circular and/or elliptical domains. In summary, for both the ES and EE conditions, where the coating solution was preheated to 70° C. prior to coating on a substrate, no hydrated domains were observed at a 200× magnification. Furthermore, regardless of the drying temperature used for the coated film, when the coating solution was not preheated (conditions SS and SE), the hydrated structures were observed. Therefore, it is likely that preheating the coating solution effectively inhibits the hydrophilic and hydrophobic segments of the polyurethane from segregating into large domains.

TABLE 1

| Coating Condition | Result |
| --- | --- |
| SS | − |
| SE | − |
| ES (Inventive) | + |
| EE (Inventive) | + |

Example 3

Figure 6:
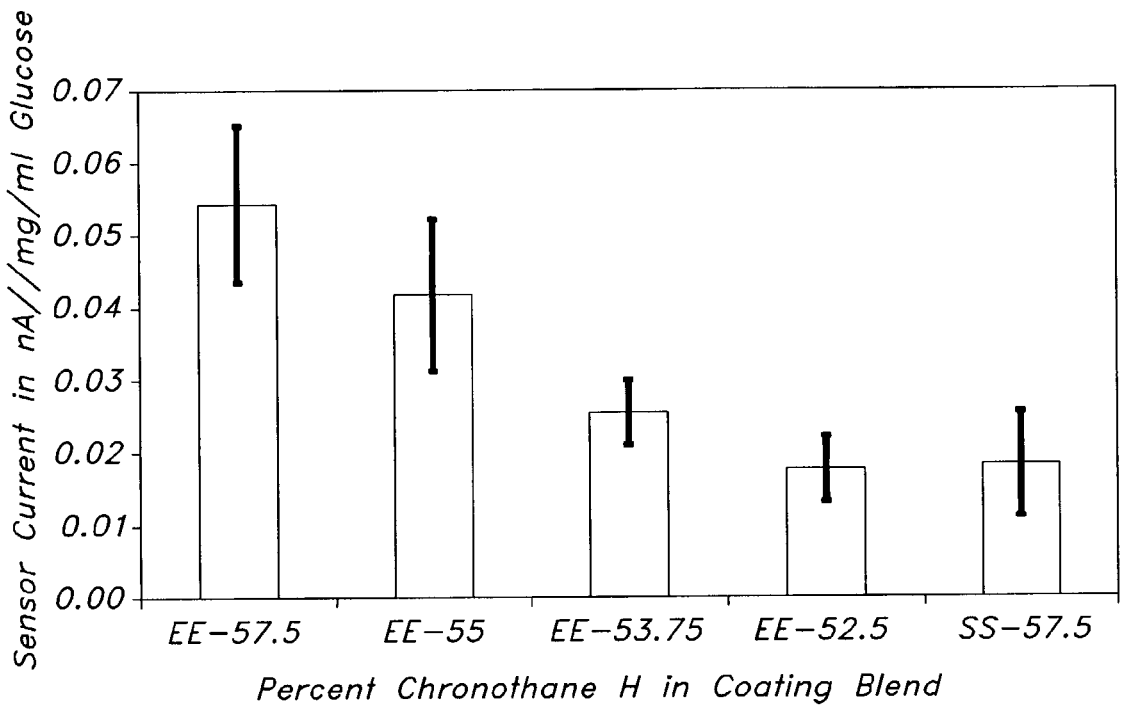
FIG. 6 is a graph showing sensor output versus the percent of the hydrophobic-hydrophilic copolymer component in the coating blend.

Evaluation of the Inventive Membranes for Their Permeability to Glucose and $H_2O_2$ Membranes prepared under the EE condition described in Example 2 were evaluated for their ability to allow glucose and hydrogen peroxide to get through the membrane to a sensor. In particular, a series of polyurethane blends of the present invention were generated wherein the percentage of Chronothane H in a coating blend was varied. Furthermore, one of these blends (57.5% Chronothane H in coating blend) was prepared under both the EE condition and the SS condition as described in Example 2. FIG. 6 shows that the sensor output generated with a series of polyurethane blends of the present invention was dependent upon the percentage of the Chronothane H. In particular, the sensor output increased as the percentage of Chronothane H in the coating blend increased. With further reference to FIG. 6, when the percentage of Chronothane H in the coating blend was 57.5%, the sensor output was three times greater for the membrane prepared under the optimized EE coating condition as compared to the non-optimized SS coating condition.

Figure 7:
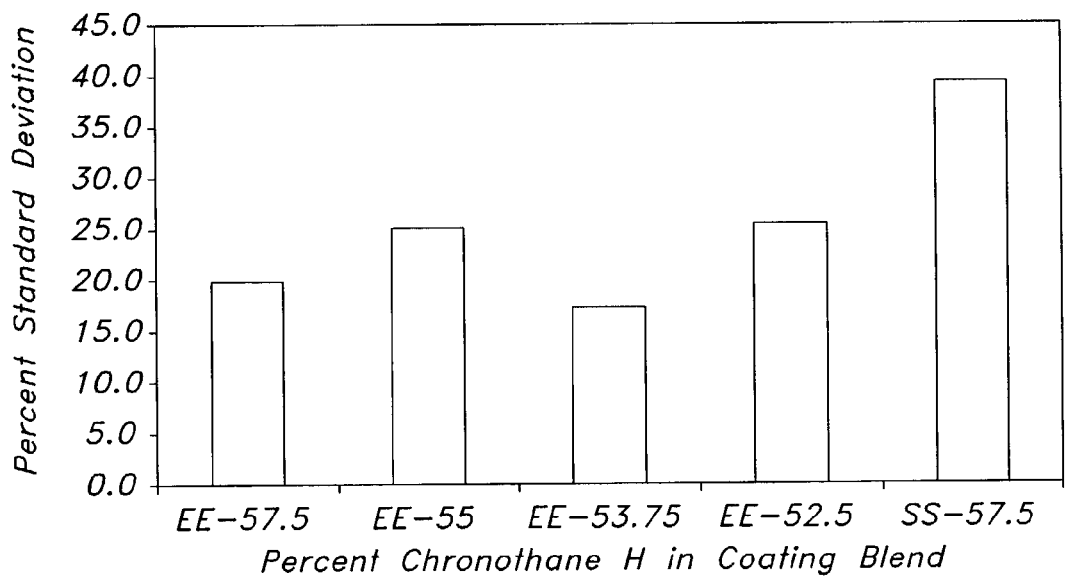
FIG. 7 is a graph showing the percent standard deviation of the sensor current versus the percent of the hydrophobic-hydrophilic copolymer component in the coating blend.

Furthermore, FIG. 7 demonstrates that, regardless of the percent Chronothane H in the coating blend, an inventive membrane prepared under the EE condition shows a fairly constant percent standard deviation of sensor output. Moreover, a membrane prepared with 57.5% Chronothane H in the coating blend under the SS condition showed a percent standard deviation of sensor output approximately twice that of an EE membrane prepared with the same percentage of Chronothane H in the blend. It is noted that given that the sensor output is a true measure of the amount of glucose getting through the membrane to the sensor, the results indicate that the permeability of glucose and $H_2O_2$ is relatively constant throughout a given inventive membrane prepared under optimized coating conditions (i.e., EE conditions). This is important from a manufacturing standpoint.

Having described the particular, preferred embodiments of the invention herein, it should be appreciated that modifications may be made therethrough without departing from the contemplated scope of the invention. The true scope of the invention is set forth in the claims appended hereto.

What is claimed is:

1. A method for preparing an implantable homogeneous membrane, the method comprising the steps of:
    forming a composition comprising a dispersion of a hydrophobic-hydrophilic polymer within a matrix of a hydrophobic polymer;
    maintaining the composition at a temperature sufficient to maintain solubility of the hydrophobic-hydrophilic polymer and the hydrophobic polymer;
    applying the composition at the temperature to a substrate to form a film thereon; and drying the film to form a membrane.

2. The method of claim 1, wherein the composition forming step comprises forming a mixture or a blend.

3. The method of claim 1, wherein the maintaining step comprises heating the composition at a temperature of about 70° C.

4. The method of claim 1, wherein the drying step comprises drying at a temperature of from about 120° C. to about 150° C.

5. The method of claim 1, wherein the hydrophobic-hydrophilic polymer comprises polyethylene oxide.

6. The method of claim 1, wherein the hydrophobic polymer comprises polyurethane.

* * * * *

US007226978C1

(12) EX PARTE REEXAMINATION CERTIFICATE (8457th)
United States Patent
Tapsak et al.

(10) Number: US 7,226,978 C1
(45) Certificate Issued: Aug. 9, 2011

(54) TECHNIQUES TO IMPROVE POLYURETHANE MEMBRANES FOR IMPLANTABLE GLUCOSE SENSORS

(75) Inventors: Mark A. Tapsak, San Diego, CA (US); Rathbun K. Rhodes, Madison, WI (US); Mark C. Shults, Madison, WI (US); Jason D. McClure, San Diego, CA (US)

(73) Assignee: DexCom, Inc., San Diego, CA (US)

Reexamination Request:
No. 90/011,329, Nov. 12, 2010

Reexamination Certificate for:
Patent No.: 7,226,978
Issued: Jun. 5, 2007
Appl. No.: 10/153,356
Filed: May 22, 2002

(51) Int. Cl.
*A61B 5/145* (2006.01)
*A61B 5/1473* (2006.01)
*B01D 39/14* (2006.01)
*B01D 69/14* (2006.01)
*B01D 71/54* (2006.01)
*B01D 71/80* (2006.01)
*C08F 265/10* (2006.01)
*C12M 1/40* (2006.01)
*C12Q 1/00* (2006.01)
*C12Q 1/54* (2006.01)
*G01N 27/28* (2006.01)
*G01N 27/30* (2006.01)
*G01N 27/327* (2006.01)
*G01N 27/416* (2006.01)

(52) U.S. Cl. .............. 525/296; 210/500.21; 210/500.27; 210/500.34; 424/424; 427/2.11; 525/420; 525/424; 525/452; 525/453; 525/474; 604/891.1

(58) Field of Classification Search .............. 521/50
See application file for complete search history.

(56) References Cited

U.S. PATENT DOCUMENTS

| | | | |
|---|---|---|---|
| 3,562,352 A | 2/1971 | Nyilas | |
| 3,898,984 A | 8/1975 | Mandel et al. | |
| 3,943,918 A | 3/1976 | Lewis | |
| 4,136,250 A | 1/1979 | Mueller et al. | |
| 4,253,469 A | 3/1981 | Aslan | |
| 4,292,423 A | 9/1981 | Kaufmann et al. | |
| 4,403,984 A | 9/1983 | Ash et al. | |
| 4,493,714 A | 1/1985 | Ueda et al. | |
| 4,494,950 A | 1/1985 | Fischell | |
| 4,527,999 A | 7/1985 | Lee | |
| 4,534,355 A | 8/1985 | Potter | |
| 4,545,382 A | 10/1985 | Higgins et al. | |
| 4,554,927 A | 11/1985 | Fussell | |
| 4,577,642 A | 3/1986 | Stokes | |
| 4,602,922 A | 7/1986 | Cabasso et al. | |
| 4,632,968 A | 12/1986 | Yokota et al. | |
| 4,644,046 A | 2/1987 | Yamada | |
| 4,647,643 A | 3/1987 | Zdrahala et al. | |
| 4,672,970 A | 6/1987 | Uchida et al. | |
| 4,680,268 A | 7/1987 | Clark, Jr. | |
| 4,684,538 A | 8/1987 | Klemarczyk | |
| 4,685,463 A | 8/1987 | Williams | |
| 4,686,137 A | 8/1987 | Ward, Jr. et al. | |
| 4,689,149 A | 8/1987 | Kanno et al. | |
| 4,711,245 A | 12/1987 | Higgins | |
| 4,721,677 A | 1/1988 | Clark | |
| 4,726,381 A | 2/1988 | Jones | |
| 4,731,726 A | 3/1988 | Allen | |
| 4,763,658 A | 8/1988 | Jones | |
| 4,781,733 A | 11/1988 | Babcock et al. | |
| 4,786,657 A | 11/1988 | Hammar et al. | |
| 4,793,555 A | 12/1988 | Lee et al. | |
| 4,795,542 A | 1/1989 | Ross et al. | |
| 4,798,876 A | 1/1989 | Gould et al. | |
| 4,805,625 A | 2/1989 | Wyler | |
| 4,822,336 A | 4/1989 | DiTraglia | |
| 4,849,458 A | 7/1989 | Reed et al. | |
| 4,852,573 A | 8/1989 | Kennedy | |
| 4,880,883 A | 11/1989 | Grasel et al. | |
| 4,886,740 A | 12/1989 | Vadgama | |
| 4,908,208 A | 3/1990 | Lee et al. | |
| 4,909,908 A | 3/1990 | Ross et al. | |
| 4,919,141 A | 4/1990 | Zier et al. | |
| 4,951,657 A | 8/1990 | Pfister et al. | |
| 4,953,552 A | 9/1990 | DeMarzo | |
| 4,970,145 A | 11/1990 | Bennetto et al. | |
| 4,973,320 A | 11/1990 | Brenner et al. | |
| 4,974,929 A | 12/1990 | Curry | |
| 4,984,929 A | 1/1991 | Rock et al. | |
| 5,002,590 A | 3/1991 | Friesen et al. | |
| 5,034,461 A | 7/1991 | Lai et al. | |
| 5,050,612 A | 9/1991 | Matsumura | |

(Continued)

FOREIGN PATENT DOCUMENTS

| | | |
|---|---|---|
| EP | 0098592 | 1/1984 |
| EP | 0127958 | 12/1984 |
| EP | 0291130 | 11/1988 |

(Continued)

OTHER PUBLICATIONS

Armour et al., Dec. 1990. Application of Chronic Intravascular Blood Glucose Sensor in Dogs, Diabetes 39:1519–1526.
Belluci et al. Jan. 1986. Electrochemical behavior of graphite–epoxy composite materials (GECM) in aqueous salt solutions, Journal of Applied Electrochemistry, 16(1):15–22.
Bindra et al. 1991. Design and In Vitro Studies of a Needle–Type Glucose Senso for Subcutaneous Monitoring. Anal. Chem 63:1692–96.

(Continued)

*Primary Examiner*—Dwayne Jones

(57) ABSTRACT

The invention provides an implantable membrane for regulating the transport of analytes therethrough that includes a matrix including a first polymer; and a second polymer dispersed throughout the matrix, wherein the second polymer forms a network of microdomains which when hydrated are not observable using photomicroscopy at 400x magnification or less. In one aspect, the homogeneous membrane of the present invention has hydrophilic domains dispersed substantially throughout a hydrophobic matrix to provide an optimum balance between oxygen and glucose transport to an electrochemical glucose sensor.

U.S. PATENT DOCUMENTS

| | | |
|---|---|---|
| 5,063,081 A | 11/1991 | Cozzette et al. |
| 5,070,169 A | 12/1991 | Robertson et al. |
| 5,071,452 A | 12/1991 | Avrillon et al. |
| 5,120,813 A | 6/1992 | Ward, Jr. |
| 5,128,408 A | 7/1992 | Tanaka et al. |
| 5,137,028 A | 8/1992 | Nishimura |
| 5,140,985 A | 8/1992 | Schroeder et al. |
| 5,155,149 A | 10/1992 | Atwater et al. |
| 5,169,906 A | 12/1992 | Cray et al. |
| 5,183,549 A | 2/1993 | Joseph et al. |
| 5,200,051 A | 4/1993 | Cozzette et al. |
| 5,202,261 A | 4/1993 | Musho et al. |
| 5,208,313 A | 5/1993 | Krishnan |
| 5,212,050 A | 5/1993 | Mier et al. |
| 5,221,724 A | 6/1993 | Li et al. |
| 5,242,835 A | 9/1993 | Jensen |
| 5,250,439 A | 10/1993 | Musho et al. |
| 5,264,104 A | 11/1993 | Gregg et al. |
| 5,269,891 A | 12/1993 | Colin |
| 5,284,140 A | 2/1994 | Allen et al. |
| 5,286,364 A | 2/1994 | Yacynych et al. |
| 5,296,144 A | 3/1994 | Sternina et al. |
| 5,299,571 A | 4/1994 | Mastrototaro |
| 5,316,008 A | 5/1994 | Suga et al. |
| 5,331,555 A | 7/1994 | Hashimoto et al. |
| 5,342,693 A | 8/1994 | Winters et al. |
| 5,352,348 A | 10/1994 | Young et al. |
| 5,387,327 A | 2/1995 | Khan |
| 5,390,671 A | 2/1995 | Lord et al. |
| 5,426,158 A | 6/1995 | Mueller et al. |
| 5,462,051 A | 10/1995 | Oka et al. |
| 5,466,575 A | 11/1995 | Cozzette et al. |
| 5,494,562 A | 2/1996 | Maley et al. |
| 5,497,772 A | 3/1996 | Schulman et al. |
| 5,507,288 A | 4/1996 | Bocker et al. |
| 5,513,636 A | 5/1996 | Palti |
| 5,521,273 A | 5/1996 | Yilgor et al. |
| 5,541,305 A | 7/1996 | Yokota et al. |
| 5,568,806 A | 10/1996 | Cheney, II et al. |
| 5,582,184 A | 12/1996 | Erickson et al. |
| 5,586,553 A | 12/1996 | Halili et al. |
| 5,611,900 A | 3/1997 | Worden et al. |
| 5,624,537 A | 4/1997 | Turner et al. |
| 5,665,222 A | 9/1997 | Heller et al. |
| 5,695,623 A | 12/1997 | Michel et al. |
| 5,703,359 A | 12/1997 | Wampler, III |
| 5,743,262 A | 4/1998 | Lepper, Jr. et al. |
| 5,746,898 A | 5/1998 | Preidel |
| 5,760,155 A | 6/1998 | Mowrer et al. |
| 5,795,453 A | 8/1998 | Gilmartin |
| 5,800,420 A | 9/1998 | Gross et al. |
| 5,807,375 A | 9/1998 | Gross et al. |
| 5,834,583 A | 11/1998 | Hancock et al. |
| 5,837,454 A | 11/1998 | Cozzette et al. |
| 5,863,972 A | 1/1999 | Beckelmann et al. |
| 5,931,814 A | 8/1999 | Alex et al. |
| 5,957,854 A | 9/1999 | Besson et al. |
| 5,961,451 A | 10/1999 | Reber et al. |
| 5,972,199 A | 10/1999 | Heller |
| 5,995,860 A | 11/1999 | Sun et al. |
| 6,002,954 A | 12/1999 | Van Antwerp et al. |
| 6,007,845 A | 12/1999 | Domb |
| 6,018,013 A | 1/2000 | Yoshida et al. |
| 6,022,463 A | 2/2000 | Leader et al. |
| 6,030,827 A | 2/2000 | Davis et al. |
| 6,043,328 A | 3/2000 | Domschke et al. |
| 6,059,946 A | 5/2000 | Yukawa et al. |
| 6,071,406 A | 6/2000 | Tsou |
| 6,091,975 A | 7/2000 | Daddona et al. |
| 6,093,172 A | 7/2000 | Funderburk et al. |
| 6,121,009 A | 9/2000 | Heller et al. |
| 6,122,536 A | 9/2000 | Sun et al. |
| 6,134,461 A | 10/2000 | Say et al. |
| 6,200,772 B1 | 3/2001 | Vadgama et al. |
| 6,271,332 B1 | 8/2001 | Lohmann et al. |
| 6,312,706 B1 | 11/2001 | Lai et al. |
| 6,343,225 B1 | 1/2002 | Clark, Jr. |
| 6,395,325 B1 | 5/2002 | Hedge et al. |
| 6,407,195 B2 | 6/2002 | Sherman et al. |
| 6,413,393 B1 | 7/2002 | Van Antwerp et al. |
| 6,424,847 B1 | 7/2002 | Mastrototaro et al. |
| 6,442,413 B1 | 8/2002 | Silver |
| 6,484,046 B1 | 11/2002 | Say et al. |
| 6,512,939 B1 | 1/2003 | Colvin et al. |
| 6,613,379 B2 | 9/2003 | Ward et al. |
| 6,642,015 B2 | 11/2003 | Vachon et al. |
| 6,654,625 B1 | 11/2003 | Say et al. |
| 6,689,265 B2 | 2/2004 | Heller et al. |
| 6,721,587 B2 | 4/2004 | Gough |
| 6,784,274 B2 | 8/2004 | van Antwerp et al. |
| 6,801,041 B2 | 10/2004 | Karinka et al. |
| 6,862,465 B2 | 3/2005 | Shults et al. |
| 6,881,551 B2 | 4/2005 | Heller et al. |
| 6,895,263 B2 | 5/2005 | Shin et al. |
| 6,895,265 B2 | 5/2005 | Silver |
| 6,931,327 B2 | 8/2005 | Goode et al. |
| 7,008,979 B2 * | 3/2006 | Schottman et al. |
| 7,033,322 B2 * | 4/2006 | Silver |
| 7,074,307 B2 * | 7/2006 | Simpson et al. |
| 7,110,803 B2 * | 9/2006 | Shults et al. |
| 7,120,483 B2 * | 10/2006 | Russell et al. |
| 7,136,689 B2 * | 11/2006 | Shults et al. |
| 7,192,450 B2 * | 3/2007 | Brauker et al. |
| 7,226,978 B2 * | 6/2007 | Tapsak et al. |
| 7,248,906 B2 * | 7/2007 | Dirac et al. |
| 7,279,174 B2 * | 10/2007 | Pacetti et al. |
| 7,335,286 B2 * | 2/2008 | Abel et al. |
| 7,336,984 B2 * | 2/2008 | Gough et al. |
| 7,357,793 B2 * | 4/2008 | Pacetti |
| 7,366,556 B2 * | 4/2008 | Brister et al. |
| 7,379,765 B2 * | 5/2008 | Petisce et al. |
| 2002/0018843 A1 * | 2/2002 | Van Antwerp et al. |
| 2002/0123087 A1 * | 9/2002 | Vachon et al. |
| 2002/0162792 A1 | 11/2002 | Zeft |
| 2003/0009093 A1 | 1/2003 | Silver |
| 2003/0065254 A1 * | 4/2003 | Schulman et al. |
| 2003/0069383 A1 * | 4/2003 | Van Antwerp et al. |
| 2003/0088166 A1 * | 5/2003 | Say et al. |
| 2003/0134347 A1 * | 7/2003 | Heller et al. |
| 2003/0199745 A1 * | 10/2003 | Burson et al. |
| 2003/0211050 A1 * | 11/2003 | Majeti et al. |
| 2003/0225324 A1 * | 12/2003 | Anderson et al. |
| 2003/0228681 A1 * | 12/2003 | Ritts et al. |
| 2003/0235817 A1 * | 12/2003 | Bartkowiak et al. |
| 2004/0006263 A1 * | 1/2004 | Anderson et al. |
| 2004/0063167 A1 * | 4/2004 | Kaastrup et al. |
| 2004/0111017 A1 | 6/2004 | Say et al. |
| 2004/0138543 A1 | 7/2004 | Russell et al. |
| 2004/0167801 A1 | 8/2004 | Say et al. |
| 2004/0176672 A1 | 9/2004 | Silver et al. |
| 2004/0180391 A1 | 9/2004 | Gratzl et al. |
| 2004/0224001 A1 | 11/2004 | Pacetti et al. |
| 2004/0234575 A1 | 11/2004 | Horres et al. |
| 2005/0027180 A1 | 2/2005 | Goode et al. |
| 2005/0027181 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |

| | | |
|---|---|---|
| 2005/0054909 A1 | 3/2005 | Petisce et al. |
| 2005/0056552 A1 | 3/2005 | Simpson et al. |
| 2005/0070770 A1 | 3/2005 | Dirac et al. |
| 2005/0077584 A1 | 4/2005 | Uhland et al. |
| 2005/0079200 A1 | 4/2005 | Rathenow et al. |
| 2005/0090607 A1 | 4/2005 | Tapsak et al. |
| 2005/0103625 A1 | 5/2005 | Rhodes et al. |
| 2005/0107677 A1 | 5/2005 | Ward et al. |
| 2005/0112169 A1 | 5/2005 | Brauker et al. |
| 2005/0118344 A1 | 6/2005 | Pacetti |
| 2005/0119720 A1 | 6/2005 | Gale et al. |
| 2005/0124873 A1 | 6/2005 | Shults et al. |
| 2005/0143635 A1 | 6/2005 | Kamath et al. |
| 2005/0154271 A1 | 7/2005 | Rasdal et al. |
| 2005/0154272 A1 | 7/2005 | Dirac et al. |
| 2005/0176136 A1 | 8/2005 | Burd et al. |
| 2005/0176678 A1 | 8/2005 | Horres et al. |
| 2005/0177036 A1 | 8/2005 | Shults et al. |
| 2005/0181012 A1 | 8/2005 | Saint et al. |
| 2005/0182451 A1 | 8/2005 | Griffin et al. |
| 2005/0187720 A1 | 8/2005 | Goode et al. |
| 2005/0192557 A1 | 9/2005 | Brauker et al. |
| 2005/0197554 A1 | 9/2005 | Polcha |
| 2005/0203360 A1 | 9/2005 | Brauker et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0251083 A1 | 11/2005 | Carr-Brendel et al. |
| 2006/0003398 A1 | 1/2006 | Heller et al. |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0047095 A1 | 3/2006 | Pacetti |
| 2006/0067908 A1 | 3/2006 | Ding |
| 2006/0068208 A1 | 3/2006 | Tapsak et al. |
| 2006/0078908 A1 | 4/2006 | Pitner et al. |
| 2006/0079740 A1 | 4/2006 | Silver et al. |
| 2006/0134165 A1 | 6/2006 | Pacetti |
| 2006/0142651 A1 | 6/2006 | Brister et al. |
| 2006/0155180 A1 | 7/2006 | Brister et al. |
| 2006/0171980 A1 | 8/2006 | Helmus et al. |
| 2006/0177379 A1 | 8/2006 | Asgari |
| 2006/0183871 A1 | 8/2006 | Ward et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200970 A1 | 9/2006 | Brister et al. |
| 2006/0204536 A1 | 9/2006 | Shults et al. |
| 2006/0229512 A1 | 10/2006 | Petisce et al. |
| 2006/0263839 A1 | 11/2006 | Ward et al. |
| 2006/0269586 A1 | 11/2006 | Pacetti |
| 2006/0275857 A1 | 12/2006 | Kjaer et al. |
| 2006/0275859 A1 | 12/2006 | Kjear |
| 2006/0289307 A1 | 12/2006 | Yu et al. |
| 2006/0293487 A1 | 12/2006 | Gaymans et al. |
| 2007/0007133 A1 | 1/2007 | Mang et al. |
| 2007/0032717 A1 | 2/2007 | Brister et al. |
| 2007/0032718 A1 | 2/2007 | Shults et al. |
| 2007/0038044 A1 | 2/2007 | Dobbles et al. |
| 2007/0129524 A1 | 6/2007 | Sunkara |
| 2007/0135698 A1 | 6/2007 | Shah et al. |
| 2007/0163880 A1 | 7/2007 | Woo et al. |
| 2007/0173709 A1 | 7/2007 | Petisce et al. |
| 2007/0173710 A1 | 7/2007 | Petisce et al. |
| 2007/0200267 A1 | 8/2007 | Tsai |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0233013 A1 | 10/2007 | Schoenberg |
| 2007/0275193 A1 | 11/2007 | DeSimone et al. |
| 2007/0299385 A1 | 12/2007 | Santini et al. |
| 2007/0299409 A1 | 12/2007 | Whilbourne et al. |
| 2008/0021008 A1 | 1/2008 | Pacetti et al. |
| 2008/0027301 A1 | 1/2008 | Ward et al. |
| 2008/0033269 A1 | 2/2008 | Zhang |
| 2008/0034972 A1 | 2/2008 | Gough et al. |
| 2008/0045824 A1 | 2/2008 | Tapsak et al. |

FOREIGN PATENT DOCUMENTS

| | | |
|---|---|---|
| EP | 0313951 | 5/1989 |
| EP | 0320109 | 6/1989 |
| EP | 0353328 | 2/1990 |
| EP | 0362145 | 4/1990 |
| EP | 0390390 | 10/1990 |
| GB | 2149918 | 6/1985 |
| JP | 57156004 | 9/1982 |
| JP | 57156005 | 9/1982 |
| JP | 58163402 | 9/1983 |
| JP | 58163403 | 9/1983 |
| JP | 59029693 | 2/1984 |
| JP | 59049803 | 3/1984 |
| JP | 59049805 | 3/1984 |
| JP | 59059221 | 4/1984 |
| JP | 59087004 | 5/1984 |
| JP | 59209608 | 11/1984 |
| JP | 59209609 | 11/1984 |
| JP | 59209610 | 11/1984 |
| JP | 60245623 | 12/1985 |
| JP | 61238319 | 10/1986 |
| JP | 62074406 | 4/1987 |
| JP | 62102815 | 5/1987 |
| JP | 62227423 | 10/1987 |
| JP | 63130661 | 6/1988 |
| JP | 01018404 | 1/1989 |
| JP | 01018405 | 1/1989 |
| JP | 05279447 | 10/1993 |
| JP | 8196626 | 8/1996 |
| JP | 10-026601 | 1/1998 |
| WO | WO 89/02720 | 4/1989 |
| WO | WO 93/14693 | 8/1993 |
| WO | WO 96/14026 | 5/1996 |
| WO | WO 96/25089 | 8/1996 |
| WO | WO 96/36296 | 11/1996 |
| WO | WO 97/01986 | 1/1997 |
| WO | WO 97/11067 | 3/1997 |
| WO | WO 99/56613 | 4/1999 |
| WO | WO 00/74753 | 12/2000 |

OTHER PUBLICATIONS

Bobbioni–Hasrch et al. 1993. Lifespan of subcutaneous glucose sensors and their performance during dynamic glycaemia changes in rats, J. Biomed. Eng. 15:457–463.

Bowman, L.; Meindl, J. D. 1986. The packaging of implantable integrated sensors. IEEE Trans Biomed Eng BME33(2):248–255.

Brooks et al. Development of an on–line glucose sensor for fermentation monitoring, Biosensors, 3:45–56 (1987/88).

Cass et al. 1984. Ferrocene–mediated enzyme electrodes for amperometric determination of glucose, Anal. Chem., 36:667–71.

Chatterjee et al. 1997. Poly(ether Urethane) and poly(ether urethane urea) membranes with high H2S/CH4 selectivity, Journal of Membrane Science 135:99–106.

Davies, et al. 1992. Polymer membranes in clinical sensor applications. I. An overview of membrane function, Biomaterials, 13(14):971–978.

Heller. 1990. Electrical wiring of redox enzymes, Acc. Chem. Res., 23:128–134.

Heller, A. 1992. Electrical Connection of Enzyme Redox Centers to Electrodes, J. Phys. Chem. 96:3579–3587.

Hicks, 1985. In Situ Monitoring, Clinical Chemistry, 31(12):1931–1935.

Hu, et al. 1993. A needle–type enzyme–based lactate sensor for in vivo monitoring, Analytica Chimica Acta, 281:503–511.

Kawagoe et al. 1991. Enzyme–modified organic conducting salt microelectrode, Anal. Chem. 63:2961–2965.

Kemer et al., 1993. The function of a hydrogen peroxide–detecting electroenzymatic glucose electrode is markedly impaired in human sub–cutaneous tissue and plasma, Biosensors & Bioelectronics, 8:473–482.

Lewis, Richard J., Sr. (Ed.), Block Polymer, Hawley's Condensed Chemical Dictionary (14th Edition), John Wiley & Sons, 2002, 1 page.

Maidan et al., 1992 Elimanation of Electrooxidizable Interferent–Produced Currents in Amperometric Biosensors, Analytical Chemistry, 64:2889–2896.

Mastrototaro et al. 1991. An electroenzymatic glucose sensor fabricated on a flexible substrate, Sensors and Actuators B, 5:139–44.

McKean, et al. Jul. 7, 1988. A Telemetry Instrumentation System for Chronically Implantation Glucose and Oxygen Sensors. Transactions on Biomedical Engineering 35:526–532.

Miller et al., 1989. Generation of IL1–like activity in response to biomedical polymer implants: a comparison of in vitro and in vivo models. J Biomed Mater Res 23:1007–1026.

Moatti–Sirat et al. 1992. Towards continuous glucose monitoring: in vivo evaluation of a miniaturized glucose sensor implanted for several days in rat subcutaneous tissue. Diabetologia 35:224–230.

Murphy, et al. 1992 Polymer membranes in clinical sensor applications, I. The design and fabrication of permselective hydrogels for electrochemical devices, Biomaterials, 13(14):979–990.

Ohara, et al. Dec. 1993. Glucose electrodes based in cross–linked bis(2,2'–bipyridine)chloroosmium(+/2+) complexed poly(1–vinylimidazole) films, Analytical Chemistry, 65:3512–3517.

Pegoraro et al. 1995. Gas transport properties of siloxane polyurethanes, Journal of Applied Polymer Science, 57:421–429.

Pickup et al. 1987/88 Implantable glucose sensors: choosing the appropriate sensing strategy, Biosensors, 3:335–346.

Pickup et al. 1989. In vivo molecular sensing in diabetes mellitus: an implantable glucose sensor with direct electron transfer Diabetologia, 32:213–217.

Pishko et al. 1991. Amperometric glucose microelectrodes prepared through immobilization of glucose oxidase in redox hydrogels, Anal. Chem., 63:2268–72.

Poitout, et al. 1991. In Vitro and In Vivo Evaluation in Dogs of a Miniaturized Glucose Sensor, ASAIO Transactions, 37:M298–M300.

Reach et al. 1992. Can continuous glucose monitoring be used for the treatment of diabetes? Analytical Chemistry 64(5):381–386.

Rebrin et al. 1989 Automated feedback control of subcutaneous glucose concentration in diabetic dogs, Diabetologia, 32:573–76 (1989).

Rinken et al. 1998. Calibration of glucose biosensors by using pre–steady state kinetic data. Biosensors & Bioelectronics, 13:801–807.

Sakakida et al. 1993. Ferrocene—Mediated Needle Type Glucose Sensor Covered with Newly Designed Biocompatible Membran, Sensors and Actuators B13–14:319–322.

Shaw et al. 1991. "In vitro testing of a simply constructed, highly stable glucose sensor suitable for implantation in diabetic patients," Biosensors & Bioelectronics, 6:401–406.

Shichiri et al. 1985. Needle–type GlucoseSensor for Wearable Artificial Endocrine Pancreas in Implantable Sensors 197–210.

Shichiri et al. 1986. Telemetry Glucose Monitoring Device with Needle–Type Glucose Sensor: A Useful Tool for Blood Glucose Monitoring in Diabetic Individuals, Diabetes Care, Inc. 9(3):298–301.

Shichiri et al. 1989. Membrane Design For Extending the Long–Life of an Implantable Glucose Sensor. Diab. Nutr. Metab. 2:309–313.

Sokol et al., 1980, Immobilized–enzyme rate–determination method for glucose analysis, Clin. Chem. 26(1):89–92.

Sternberg et al. 1988. Study and Development of Multilayer Needle–type Enzyme–based Glucose Microsensors. Biosensors 4:27–40.

Takegami et al. 1992. Pervaporation of ethanol water mixtures using novel hydrophobic membranes containing polydimethylsilixane, Journal of Membrane Science, 75(93–105).

Thomas et al. 2001. In vitro studies on the effect of physical cross–linking on the biological performance of aliphatic poly(urethane use) for blood contact applications. Biomacromol. 2(2); 588–596.

Thompson et al. 1986. In Vivo Probes: Problems and Perspectives, Department of Chemistry, University of Toronto, Canada, pp. 255–261.

Turner et al. 1985. Diabetes mellitus: biosensors for research and management, Biosensors, 1:85–115.

Velho et al. 1989. Strategies for calibrating a subcutaneous glucose sensor. Biomed Biochim Acta 48(11/12):957–964.

von Woedtke et al. 1989. In situ calibration of implanted electrochemical glucose sensors. Biomed Biochim. Acta 48(11/12):943–952.

Wilson et al. 1992. Progress toward the development of an implantable sensor for glucose. Clin. Chem. 38(9):1613–1617.

Notice of Reasons for Rejection dated Jan. 27, 2009 in Japanese App. No. 2004–507523.

EPO Communication dated Mar. 3, 2008 in EP Application No. 03726922.2 filed May 20, 2003.

EPO Communication dated Jun. 30, 2009 in EP Application No. 03726922.2 filed May 20, 2003.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 5 are determined to be patentable as amended.

Claims 2-4 and 6, dependent on an amended claim, are determined to be patentable.

New claim 7 added and determined to be patentable.

1. A method for preparing an implantable homogeneous membrane, the method comprising the steps of: forming a composition comprising a dispersion of a hydrophobic-hydrophilic [polymer] *copolymer* within a matrix of a hydrophobic polymer; maintaining the composition at a temperature sufficient to maintain solubility of the hydrophobic-hydrophilic [polymer] *copolymer* and the hydrophobic polymer, applying the composition at the temperature to a substrate to form a film thereon; and drying the film to form a membrane.

5. The method of claim 1, wherein the hydrophobic-hydrophilic [polymer] *copolymer* comprises *a hydrophilic component comprising* polyethylene oxide.

7. *The method of claim 1, wherein the membrane has an oxygen-to-glucose permeability ratio of approximately 200:1.*

\* \* \* \* \*

(12) INTER PARTES REEXAMINATION CERTIFICATE (1071st)
United States Patent
Tapsak et al.

(10) Number: US 7,226,978 C2
(45) Certificate Issued: *Mar. 17, 2015

(54) TECHNIQUES TO IMPROVE POLYURETHANE MEMBRANES FOR IMPLANTABLE GLUCOSE SENSORS

(75) Inventors: Mark A. Tapsak, San Diego, CA (US); Rathbun K. Rhodes, Madison, WI (US); Mark C. Shults, Madison, WI (US); Jason D. McClure, San Diego, CA (US)

(73) Assignee: DexCom, Inc., San Diego, CA (US)

Reexamination Request:
No. 95/002,379, Sep. 14, 2012

Reexamination Certificate for:
Patent No.: 7,226,978
Issued: Jun. 5, 2007
Appl. No.: 10/153,356
Filed: May 22, 2002

Reexamination Certificate C1 7,226,978 issued Aug. 9, 2011

(*) Notice: This patent is subject to a terminal disclaimer.

(51) Int. Cl.
| | |
|---|---|
| *C08F 265/10* | (2006.01) |
| *B01D 39/14* | (2006.01) |
| *B05D 3/00* | (2006.01) |
| *B05D 5/00* | (2006.01) |
| *C12Q 1/00* | (2006.01) |
| *A61B 5/1473* | (2006.01) |
| *B01D 69/14* | (2006.01) |
| *A61B 5/145* | (2006.01) |
| *B01D 71/80* | (2006.01) |
| *B01D 71/54* | (2006.01) |

(52) U.S. Cl.
CPC *B05D 3/007* (2013.01); *B05D 5/00* (2013.01); *C12Q 1/002* (2013.01); *A61B 5/1473* (2013.01); *B01D 69/141* (2013.01); *A61B 5/14532* (2013.01); *B01D 71/80* (2013.01); *B01D 71/54* (2013.01)
USPC ............... 525/296; 210/500.21; 210/500.27; 210/500.34; 424/424; 427/2.11; 525/420; 525/424; 525/452; 525/453; 525/474; 604/891.1

(58) Field of Classification Search
None
See application file for complete search history.

(56) References Cited

To view the complete listing of prior art documents cited during the proceeding for Reexamination Control Number 95/002,379, please refer to the USPTO's public Patent Application Information Retrieval (PAIR) system under the Display References tab.

*Primary Examiner* — Dwayne Jones

(57) ABSTRACT

The invention provides an implantable membrane for regulating the transport of analytes therethrough that includes a matrix including a first polymer; and a second polymer dispersed throughout the matrix, wherein the second polymer forms a network of microdomains which when hydrated are not observable using photomicroscopy at 400x magnification or less. In one aspect, the homogeneous membrane of the present invention has hydrophilic domains dispersed substantially throughout a hydrophobic matrix to provide an optimum balance between oxygen and glucose transport to an electrochemical glucose sensor.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-7, dependent on an amended claim, are determined to be patentable.

New claims 8-37 are added and determined to be patentable.

1. A method for preparing an implantable homogeneous membrane, the method comprising the steps of:
   forming a composition comprising a dispersion of a hydrophobic-hydrophilic copolymer within a matrix of a hydrophobic polymer;
   maintaining the composition at [a] *an elevated* temperature *above room temperature* sufficient to maintain solubility of the hydrophobic-hydrophilic copolymer and the hydrophobic polymer;
   applying the composition at the *elevated* temperature to a substrate to form a film thereon; and
   drying the film to form a membrane.

*8. The method of claim 1, wherein the hydrophobic polymer comprises polysiloxanes or polycarbosiloxanes.*

*9. The method of claim 1, wherein the substrate comprises an electrode.*

*10. The method of claim 1, wherein the hydrophobic-hydrophilic copolymer has a ratio of hydrophobic component to hydrophilic component of from 70:30 to 90:10.*

*11. The method of claim 1, wherein the hydrophobic-hydrophilic copolymer and the hydrophobic polymer are soluble with each other at the elevated temperature.*

*12. The method of claim 1, wherein the composition further comprises a solvent.*

*13. A method for preparing an implantable homogeneous enzyme-containing glucose sensor membrane, the method comprising the steps of:*
   *forming a composition comprising a dispersion of a hydrophobic-hydrophilic copolymer within a matrix of a hydrophobic polymer;*
   *maintaining the composition at a temperature sufficient to maintain solubility of the hydrophobic-hydrophilic copolymer and the hydrophobic polymer;*
   *applying the composition at the temperature to a substrate to form a film thereon, wherein the substrate comprises an enzyme-containing layer; and*
   *drying the film to form the enzyme-containing glucose sensor membrane.*

*14. The method of claim 13, wherein the hydrophobic-hydrophilic copolymer and the hydrophobic polymer are soluble with each other at the temperature.*

*15. The method of claim 13, wherein the substrate comprises an electrode.*

*16. The method of claim 15, wherein the enzyme-containing layer is sufficiently permeable to permit passage of hydrogen peroxide to the electrode surface.*

*17. The method of claim 13, wherein the enzyme-containing layer comprises immobilized enzymes configured to promote a reaction between glucose and oxygen.*

*18. The method of claim 13, wherein the maintaining step comprises maintaining the composition at an elevated temperature above room temperature.*

*19. The method of claim 13, wherein the composition further comprises a solvent.*

*20. The method of claim 13, wherein the enzyme-containing membrane has an oxygen-to-glucose permeability ratio of approximately 200:1.*

*21. A method for preparing an implantable homogeneous membrane, the method comprising the steps of:*
   *forming a composition comprising a dispersion of a hydrophobic-hydrophilic copolymer within a matrix of a hydrophobic polymer;*
   *maintaining the composition at a temperature sufficient to maintain solubility of the hydrophobic-hydrophilic copolymer and the hydrophobic polymer;*
   *applying the composition at the temperature to a substrate to form a film thereon; and*
   *drying the film to form a membrane, wherein the hydrophobic-hydrophilic copolymer forms a network of microdomains, wherein the microdomains are substantially uniform in size and are substantially distributed throughout the membrane.*

*22. The method of claim 21, wherein the microdomains are not observable at 400x magnification or less.*

*23. The method of claim 21, wherein the hydrophobic-hydrophilic copolymer comprises polyethylene oxide.*

*24. The method of claim 21, wherein the hydrophobic polymer comprises polyurethane.*

*25. The method of claim 21, wherein the hydrophobic polymer comprises polysiloxanes or polycarbosiloxanes.*

*26. The method of claim 21, wherein the hydrophobic-hydrophilic copolymer has a ratio of hydrophobic component to hydrophilic component of from 70:30 to 90:10.*

*27. The method of claim 21, wherein the composition further comprises a solvent.*

*28. The method of claim 21, wherein the substrate comprises an electrode.*

*29. A method for preparing an implantable homogeneous continuous glucose sensor membrane, the method comprising the steps of:*
   *forming a composition comprising a dispersion of a hydrophobic-hydrophilic copolymer within a matrix of a hydrophobic polymer by dispersing hydrophobic-hydrophilic copolymer and hydrophobic polymer in a solvent;*
   *maintaining the composition at a temperature sufficient to maintain solubility of the hydrophobic-hydrophilic copolymer and the hydrophobic polymer;*
   *applying the composition at the temperature to a substrate to form a film thereon wherein the hydrophobic-hydrophilic copolymer is substantially dispersed throughout the composition during the applying; and*
   *drying the film to form a membrane, wherein hydrophobic-hydrophilic copolymer is substantially dispersed throughout the matrix of the hydrophobic polymer in the dried membrane.*

*30. The method of claim 29, wherein hydrophobic-hydrophilic copolymer and the hydrophobic polymer are soluble with each other at the temperature.*

*31. The method of claim 29, wherein the hydrophobic polymer comprises polyurethane.*

32. The method of claim 29, wherein the hydrophobic polymer comprises polysiloxanes or polycarbosiloxanes.

33. The method of claim 29, wherein the hydrophobic-hydrophilic copolymer comprises polyethylene oxide.

34. The method of claim 29, wherein the membrane has a thickness of from about 10 microns to about 100 microns.

35. The method of claim 29, wherein the hydrophobic-hydrophilic copolymer has a ratio of hydrophobic component to hydrophilic component of from 70:30 to 90:10.

36. The method of claim 29, wherein the substrate comprises an electrode.

37. The method of claim 21, wherein the hydrophobic-hydrophilic copolymer and the hydrophobic polymer are soluble with each other at the temperature.

* * * * *